US011324720B2

(12) United States Patent
Zhang

(10) Patent No.: US 11,324,720 B2
(45) Date of Patent: May 10, 2022

(54) ANTIPROLIFERATIVE DNA POLYMERASE INHIBITOR

(71) Applicant: NEW YORK MEDICAL COLLEGE, Valhalla, NY (US)

(72) Inventor: Zhongtao Zhang, Valhalla, NY (US)

(73) Assignee: NEW YORK MEDICAL COLLEGE, Valhalla, NY (US)

( * ) Notice: Subject to any disclaimer, the term of this patent is extended or adjusted under 35 U.S.C. 154(b) by 0 days.

(21) Appl. No.: 16/659,283

(22) Filed: Oct. 21, 2019

(65) Prior Publication Data

US 2020/0121641 A1 Apr. 23, 2020

Related U.S. Application Data

(60) Provisional application No. 62/747,771, filed on Oct. 19, 2018.

(51) Int. Cl.
    *A61K 31/381* (2006.01)
    *A61K 31/496* (2006.01)
    *A61K 31/444* (2006.01)
    *A61K 31/4436* (2006.01)

(52) U.S. Cl.
    CPC .......... *A61K 31/381* (2013.01); *A61K 31/444* (2013.01); *A61K 31/4436* (2013.01); *A61K 31/496* (2013.01)

(58) Field of Classification Search
    CPC .................................................... A61K 31/381
    See application file for complete search history.

(56) References Cited

U.S. PATENT DOCUMENTS

| 3,507,874 A | 4/1970 | Laliberte |
| 4,011,333 A | 3/1977 | Parker |

OTHER PUBLICATIONS

Zhang, Jinhui, et al. "Anti-cancer gallotannin penta-O-galloyl-beta-D-glucose is a nanomolar inhibitor of select mammalian DNA polymerases." Biochemical Pharmacology. (2010), vol. 80, pp. 1125-1132. (Year: 2010).*
Mishra, B., et al. "Discovery of a novel DNA polymerase inhibitor and characterization of its antiproliferative properties." Cancer Biology & Therapy. (2019), vol. 20, No. 4, pp. 474-486. (Year: 2019).*
Doublie, S. & Zahn, K. E. Structural insights into eukaryotic DNA replication. Frontiers in microbiology 5, 444, pp. 1-8, doi:10.3389/fmicb.2014.00444 (2014).
Zhang, D. & O'Donnell, M. The Eukaryotic Replication Machine. The Enzymes 39, 191-229, doi:10.1016/bs.enz.2016.03.004 (2016).
Johansson, E. & Macneill, S. A. The eukaryotic replicative DNA polymerases take shape. Trends in biochemical sciences 35, 339-347, doi:10.1016/j.tibs.5 2010.01.004 (2010).
Irwin, J. J. Using ZINC to acquire a virtual screening library. Current protocols in bioinformatics / editoral board, Andreas D. Baxevanis, et al. Chapter 14,Unit 14 16, doi:10.1002/0471250953.bi1406s22 (2008).
Wu, P., Nielsen, T. E. & Clausen, M. H. FDA-approved small-molecule kinase inhibitors. Trends in pharmacological sciences 36, 422-439, doi:10.1016/j.tips.2015.04.005 (2015).
Ledermann, J. et al. Olaparib maintenance therapy in patients with platinumsensitive relapsed serous ovarian cancer: a preplanned retrospective analysis of outcomes by BRCA status in a randomised phase 2 trial. The Lancet Oncology 15, 852-861, doi:10.1016/s1470-2045(14)70228-1 (2014).
George Paul, A., Sharma-Walia, N., Kerur, N., White, C. & Chandran, B. Piracy of prostaglandin E2/EP receptor-mediated signaling by Kaposi's sarcoma associated herpes virus (HHV-8) for latency gene expression: strategy of a successful pathogen. Cancer research 70, 3697-3708, doi:10.1158/0008-5472.can-09-3934 (2010).
Lee, M., Wang, X., Zhang, S., Zhang, Z. & Lee, E. Y. C. Regulation and Modulation of Human DNA Polymerase delta Activity and Function. Genes 8, doi:10.3390/genes8070190 (2017).
Maloisel, L., Fabre, F. & Gangloff, S. DNA polymerase delta is preferentially recruited during homologous recombination to promote heteroduplex DNA extension. Mol Cell Biol 28, 1373-1382, doi:10.1128/mcb.01651-07 (2008).
Ahrabi, S. et al. A role for human homologous recombination factors in suppressing microhomology-mediated end joining. Nucleic Acids Res 44, 5743-5757, doi:10.1093/nar/gkw326 (2016).
De Picciotto, N., Cacheux, W., Roth, A., Chappuis, P. O. & Labidi-Galy, S. I. Ovarian cancer: Status of homologous recombination pathway as a predictor of drug response. Critical reviews in oncology/hematology 101, 50-59, doi:10.1016/j.critrevonc.2016.02.014 (2016).
Meehan, R. S. & Chen, A. P. New treatment option for ovarian cancer: PARP inhibitors. Gynecologic oncology research and practice 3, 3, doi:10.1186/s40661-016-0024-7 (2016).
Kim, G. et al. FDA Approval Summary: Olaparib Monotherapy in Patients with Deleterious Germline BRCA-Mutated Advanced Ovarian Cancer Treated with Three or More Lines of Chemotherapy. Clinical cancer research : an officialjournal of the American Association for Cancer Research 21, 4257-4261, doi:10.1158/1078-0432.ccr-15-0887 (2015).
Moore, D. C., Ringley, J. T. & Patel, J. Rucaparib: A Poly(ADP-Ribose) Polymerase Inhibitor for BRCA-Mutated Relapsed Ovarian Cancer. Journal of pharmacy practice, 897190017743131, doi:10.1177/0897190017743131 (2017).

(Continued)

Primary Examiner — John S Kenyon
(74) Attorney, Agent, or Firm — Leason Ellis LLP

(57) ABSTRACT

Methods for inhibiting cell growth, inhibiting DNA polymerase activity, and inhibiting DNA replication and repair are provided. In a method of inhibiting cell growth, a cell, such as a cancer cell, is contacted with zelpolib or a derivative or pharmaceutically acceptable salt thereof. The cell growth can be inhibited in vivo, and in certain embodiments, the cell growth is inhibited in vitro. In a method for inhibiting DNA polymerase activity, a DNA polymerase is contacted with zelpolib or a derivative or pharmaceutically acceptable salt thereof. In certain embodiments, the DNA polymerase is Pol δ. In a method for inhibiting DNA replication and repair, a cell, such as a cancer cell, is contacted with zelpolib or a derivative or pharmaceutically acceptable salt thereof. The DNA replication and repair can be inhibited in vivo, and in certain embodiments, the DNA replication and repair is inhibited in vitro.

12 Claims, 15 Drawing Sheets

(56) References Cited

OTHER PUBLICATIONS

Figure 1A:
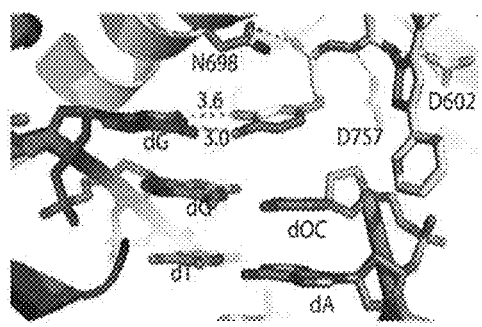

Taylor, K. N. & Eskander, R. N. PARP inhibitors in epithelial ovarian cancer. Recent patents on anti-cancer drug discovery 13, 145-158, doi:10.2174/1574892813666171204094822 (2018).
Scott, L. J. Niraparib: First Global Approval. Drugs 77, 1029-1034, doi:10.1007/s40265-017-0752-y (2017).
Syed, Y. Y. Rucaparib: First Global Approval. Drugs 77, 585-592, doi:10.1007/s40265-017-0716-2 (2017).
Damia, G. et al. Activity of aphidicolin glycinate alone or in combination with cisplatin in a murine ovarian tumor resistant to cisplatin. Cancer chemotherapy and pharmacology 30, 459-464 (1992).
Moreland, N. J., Illand, M., Kim, Y. T., Paul, J. & Brown, R. Modulation of drug resistance mediated by loss of mismatch repair by the DNA polymerase inhibitor aphidicolin. Cancer research 59, 2102-2106 (1999).
O'Dwyer, P. J. et al. Antitumor activity and biochemical effects of aphidicolin glycinate (NSC 303812) alone and in combination with cisplatin in vivo. Cancer research 54, 724-729 (1994).
Sargent, J. M., Elgie, A. W., Williamson, C. J. & Taylor, C. G. Aphidicolin markedly increases the platinum sensitivity of cells from primary ovarian tumours. British journal of cancer 74, 1730-1733 (1996).
Sessa, C. et al. Phase I and clinical pharmacological evaluation of aphidicolin glycinate. Journal of the National Cancer Institute 83, 1160-1164 (1991).
Leeds, J. M. & Mathews, C. K. Cell cycle-dependent effects on deoxyribonucleotide and DNA labeling by nucleoside precursors in mammalian cells. Mol Cell Biol 7, 532-534 (1987).
Leeds, J. M., Slabaugh, M. B. & Mathews, C. K. DNA precursor pools and ribonucleotide reductase activity: distribution between the nucleus and cytoplasm of mammalian cells. Mol Cell Biol 5, 3443-3450 (1985).
Momparler, R. L. Biochemical pharmacology of cytosine arabinoside. Medical and pediatric oncology 10 Suppl 1, 45-48 (1982).
Perrino, F. W. & Mekosh, H. L. Incorporation of cytosine arabinoside monophosphate into DNA at internucleotide linkages by human DNA polymerase alpha. J Biol Chem 267, 23043-23051 (1992).
Dietlein, F., Thelen, L. & Reinhardt, H. C. Cancer-specific defects in DNA repair pathways as targets for personalized therapeutic approaches. Trends in genetics:TIG 30, 326-339, doi:10.1016/j.tig.2014.06.003 (2014).

Prakash, R., Zhang, Y., Feng, W. & Jasin, M. Homologous recombination and human health: the roles of BRCA1, BRCA2, and associated proteins. Cold SpringHarbor perspectives in biology 7, a016600, doi:10.1101/cshperspect.a016600 (2015).
Eshleman, J. R. & Markowitz, S. D. Mismatch repair defects in human carcinogenesis. Human molecular genetics 5 Spec No. 1489-1494 (1996).
Boland, C. R. & Goel, A. Microsatellite instability in colorectal cancer. Gastroenter.
Konstantinopoulos, P. A., Ceccaldi, R., Shapiro, G. I. & D'Andrea, A. D. Homologous Recombination Deficiency: Exploiting 5 the Fundamental Vulnerability of Ovarian Cancer. Cancer discovery 5, 1137-1154,doi:10.1158/2159-8290.cd-15-0714 (2015).
Caruso, D. et al. Niraparib in ovarian cancer: results to date and clinical potential. Therapeutic advances in medical oncology 9, 579-588,doi:10.1177/1758834017718775 (2017).
Chang, L., Chang, M., Chang, H. M. & Chang, F. Microsatellite Instability: A Predictive Biomarker for Cancer Immunotherapy. Applied immunohistochemistry& molecular morphology : AIMM 26, e15-e21, doi:10.1097/pai.0000000000000575 (2018).
First Tissue-Agnostic Drug Approval Issued. Cancer discovery 7, 656, doi:10.1158/2159-8290.cd-nb2017-078 (2017).
McVey, M., Khodaverdian, V. Y., Meyer, D., Cerqueira, P. G. & Heyer, W. D. Eukaryotic DNA Polymerases in Homologous Recombination. Annual review of genetics 50, 393-421, doi:10.1146/annurev-genet-120215-035243 (2016).
Longley, M. J., Pierce, A. J. & Modrich, P. DNA polymerase delta is required for human mismatch repair in vitro. J Biol Chem 272, 10917-10921 (1997).
Swan, M. K., Johnson, R. E., Prakash, L., Prakash, S. & Aggarwal, A. K. Structural basis of high-fidelity DNA synthesis by yeast DNA polymerase delta. Nat Struct Mol Biol 16, 979-986, doi:10.1038/nsmb.1663 (2009).
Guex, N. & Peitsch, M. C. Swiss-Model and the Swiss-PdbViewer: an environment for comparative protein modeling. Electrophoresis 18, 2714-2723, doi:10.1002/elps.1150181505 (1997).
Mezencev, R., Matyunina, L. V., Wagner, G. T. & McDonald, J. F. Acquired resistance of pancreatic cancer cells to cisplatin is multifactorial with cell context dependent involvement of resistance genes. Cancer gene therapy 23, 446-453, doi:10.1038/cgt.2016.71 (2016).
Coley, H. M. Development of drug-resistant models. Methods in molecular medicine 88, 267-273 (2004).

* cited by examiner

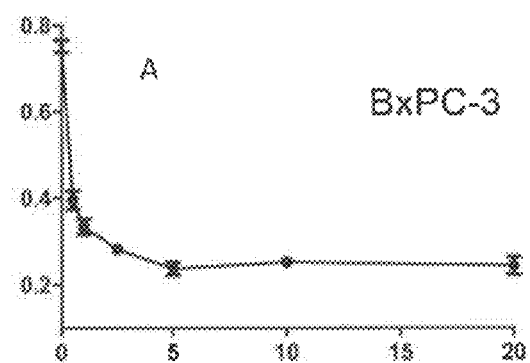
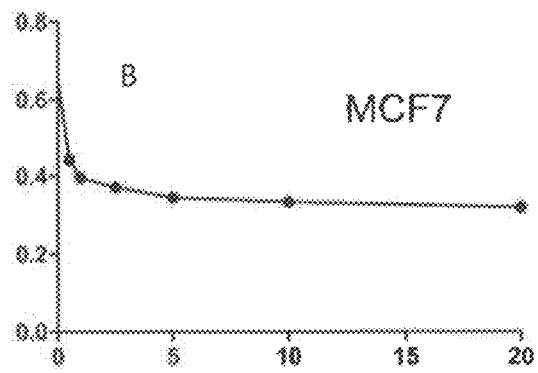
FIG. 4A	FIG. 4B
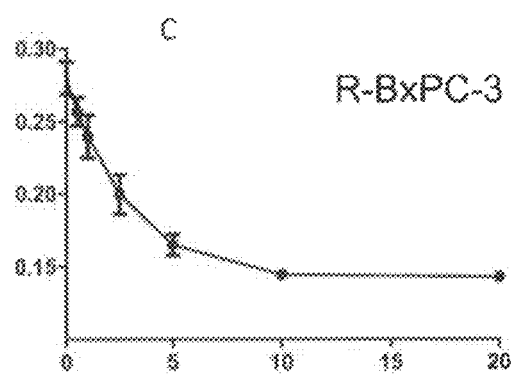
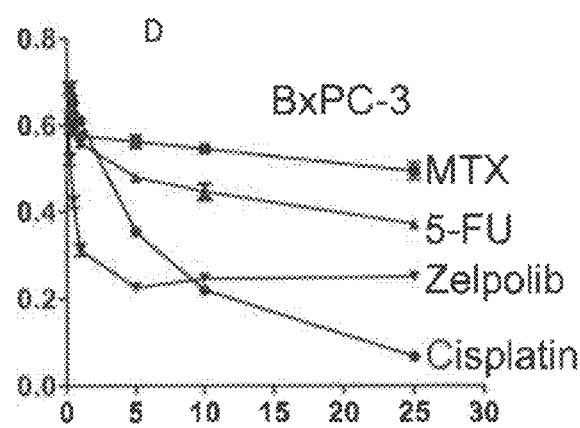
FIG. 4C	FIG. 4D

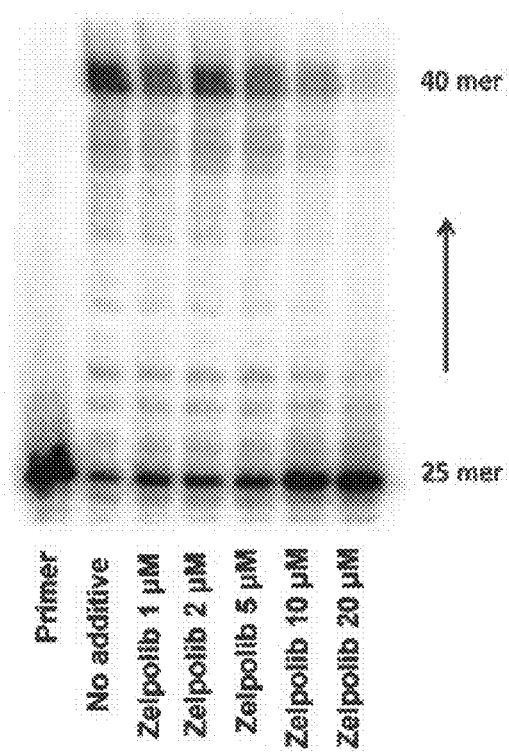
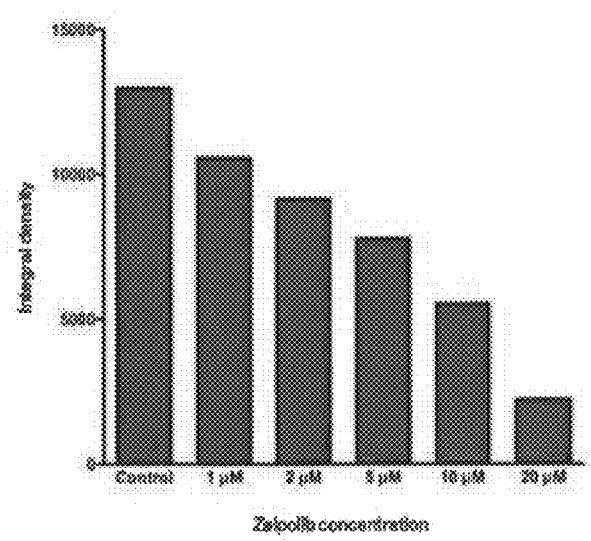
FIG. 7A          FIG. 7B

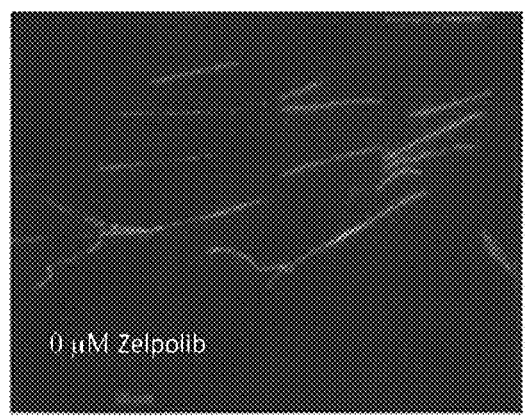
FIG. 9

ANTIPROLIFERATIVE DNA POLYMERASE INHIBITOR

CROSS REFERENCE TO RELATED APPLICATION

This application claims priority to U.S. provisional application No. 62/747,771, filed Oct. 19, 2018, the contents of which are hereby incorporated by reference in its entirety.

TECHNICAL FIELD

The present disclosure is related to methods and compositions for inhibiting cell growth, and further, methods and compositions for inhibiting the DNA replication and repair in cells such as cancer cells.

BACKGROUND OF THE DISCLOSURE

Targeting DNA replication has been the most successful approach in chemotherapy[1,2], as cancer cells, regardless of histology, will not divide without chromosome duplication. There are a number of essential enzymes and two key components for the DNA replication process and a few of these have been successfully targeted in cancer therapy. These two key components include the chromosomal template for replication and deoxynucleotides (dNTPs) for synthesizing the new copy. Key enzymes include topoisomerases[3-5] that prepares chromosome for replication, the helicase that unwinds the duplex DNA, and polymerases that synthesize the daughter strand.

The most diverse category of chemotherapeutic approach/agents directly damage the template[6], the parental chromosome, so as to prevent DNA replication. The mechanisms include crosslinking the DNA duplex by platinum derivatives, modification of bases by alkylating agents, and template breakage by radiation. However, the indiscriminate nature of this class of chemicals leads to damage to the chromosomes of all cells, even non-dividing cells. Therefore, this class of chemicals will have significant side effects and are destined to have a narrow therapeutic window[1,6].

The second class of compounds, broadly termed antimetabolites[7], target a number of pathways that lead to the synthesis of deoxynucleotides. Thus, these compounds will diminish cellular dNTP levels and prevent DNA replication. This class of agents, such as methotrexate and its analogs[8], are quite specific in targeting DNA replication, an event only present in proliferating cells. Consequently, these compounds offer a better side effect profile and can be taken for longer duration. Indeed, methotrexate is prescribed for a number of disorders related to cell proliferation and many patients have been on it for years in the case of rheumatoid arthritis. Nevertheless, the targeting of enzymes such as dihydrofolate reductase[8], thymidylate synthase[2], or ribonucleotide reductase[9] by antimetabolite, can lead to effects in other metabolic pathways other than dNTP synthesis in both proliferating and nonproliferating cells. This results in greater potential for side effects.

On the enzyme front, topoisomerases[8] have been successfully targeted. A number of inhibitors have gained FDA approval that include topotecan analogs and etoposide. However, topoisomerases are indispensable for resolution of DNA topology issues during transcription[10] as well and these inhibitors will impair many functions of all cell types and exhibit severe side effects as DNA single strand breaks or double strand breaks are induced[11].

Ostensibly missing are chemical entities that target the most important enzymes in DNA replication—DNA polymerases, even though DNA or RNA polymerases are the targets for many antiviral therapeutics. Reversible inhibitors of DNA polymerases should inhibit cancer cell proliferation and possess some advantages over DNA damaging agents and topoisomerase inhibitors. First, due to the specific function of replicative polymerases, reversible DNA polymerase inhibitors will inhibit DNA replication alone, and thus cell proliferation without affecting non-proliferating cells. Secondly, these inhibitors will not damage the chromosomes of non-dividing cells and should have minimal impact on transcription. Consequently, the side effect profile of polymerase inhibitors should be at least as good as antimetabolites exemplified by methotrexate.

These and other needs are addressed by the present application.

SUMMARY OF THE DISCLOSURE

In a first aspect, a method of inhibiting cell growth is provided. In the method of inhibiting cell growth, a cell is contacted with a compound, where the compound comprises zelpolib, a derivative of zelpolib, or a pharmaceutically acceptable salt of zelpolib.

In another aspect, the cell growth is inhibited in vivo. In another aspect, the cell growth is inhibited in vitro. In another aspect, the cell is a cancer cell.

In another aspect, the derivative of zelpolib is represented by the following formula:

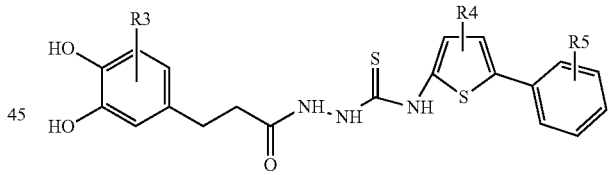

where R3, R4, and R5 is hydrogen, or a substitution for hydrogen. The substitution for hydrogen can be selected from the group of a fluoro group, a chloro group, a bromo group, a nitro group, and a sulfo group. In at least one aspect, at least one of R3, R4, and R5 is not hydrogen.

In another aspect, the derivative of zelpolib is selected from the group of compounds 8-11:

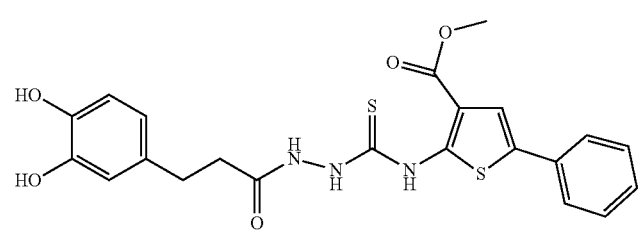

9

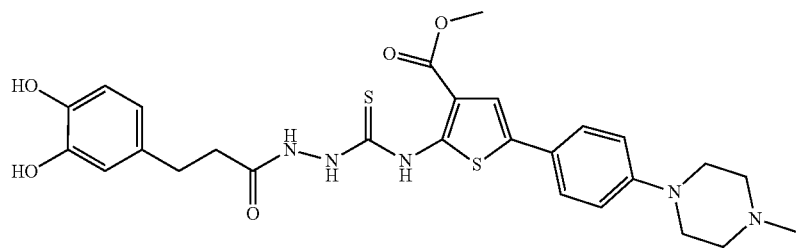

10

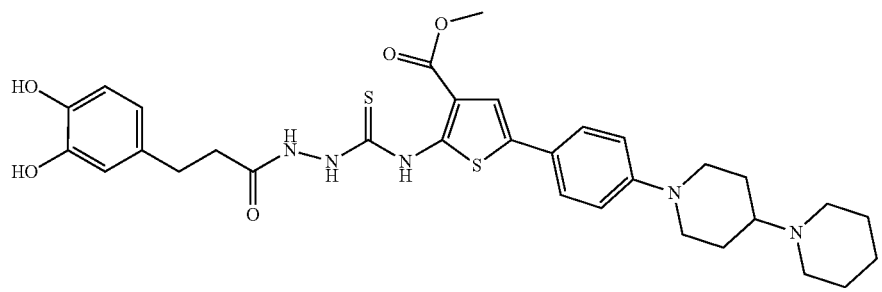

11

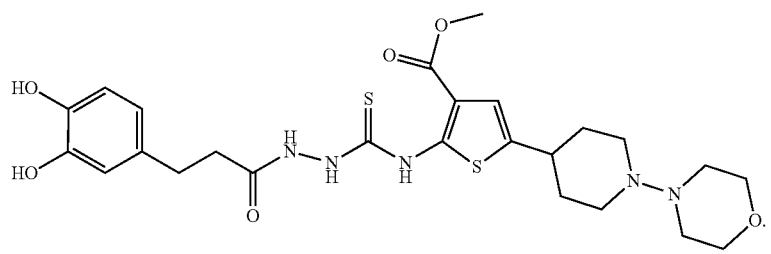

In a second aspect, a method for inhibiting DNA polymerase activity is provided. In the method for inhibiting DNA polymerase activity, a DNA polymerase is contacted with a compound, where the compound comprises zelpolib, a derivative of zelpolib, or a pharmaceutically acceptable salt of zelpolib.

In another aspect, the DNA polymerase is Pol δ. In a further aspect, activity of Pol δ is inhibited in vitro. In a further aspect, activity of Pol δ is inhibited in vitro.

In another aspect, the derivative of zelpolib is represented by the following formula:

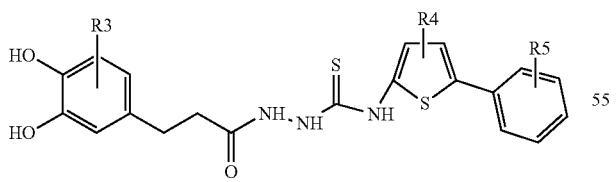

where R3, R4, and R5 is hydrogen, or a substitution for hydrogen selected from following group: a fluoro group, a chloro group, a bromo group, a nitro group, and a sulfo group. In another aspect, at least one of R3, R4, and R5 is not hydrogen.

In another aspect, the derivative of zelpolib is selected from the group consisting of compounds 8-11:

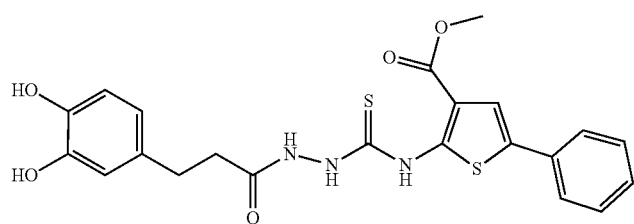

8

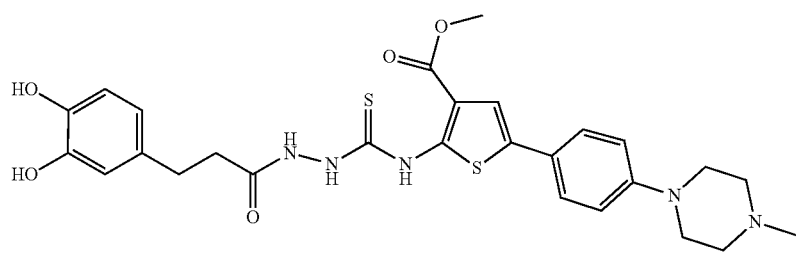

9

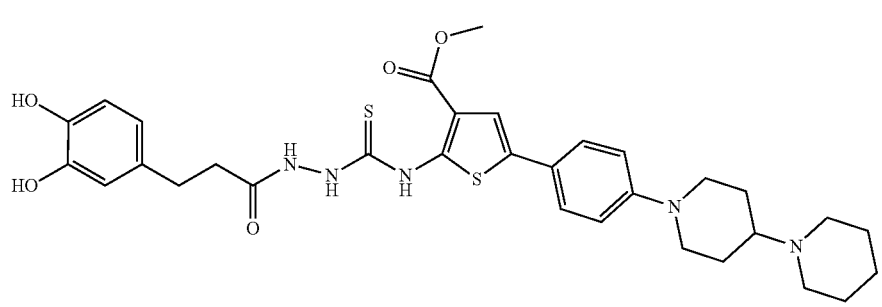

10

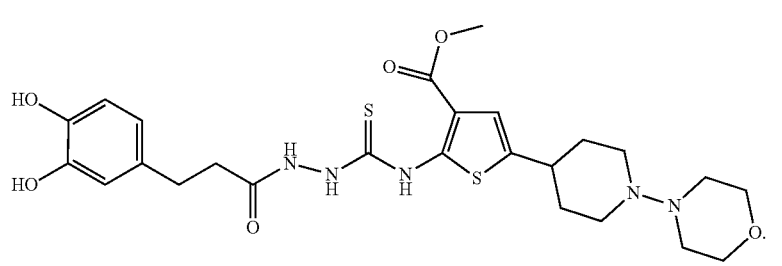

11

In a third aspect, a method for inhibiting DNA replication and DNA repair in a cell is provided. In the method for inhibiting DNA replication and repair, a cell is contacted with a compound, where the compound comprises zelpolib, a derivative of zelpolib, or a pharmaceutically acceptable salt of zelpolib.

In another aspect, DNA replication and repair is inhibited in the cell in vivo. In another aspect, DNA replication and repair is inhibited in the cell in vitro. In another aspect, the cell is a cancer cell.

In another aspect, the derivative of zelpolib is represented by the following formula:

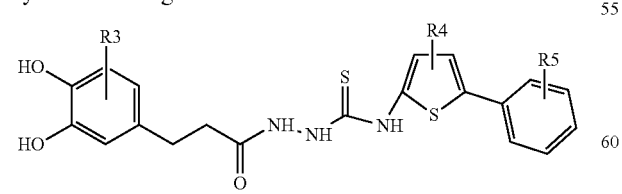

where $R_3$, $R_4$, and $R_5$ is hydrogen, or a substitution for hydrogen selected from the following group: a fluoro group, a chloro group, a bromo group, a nitro group, and a sulfo group. In at least one aspect, at least one of $R_3$, $R_4$, and $R_5$ is not hydrogen.

In another aspect, the derivative of zelpolib is selected from the group consisting of compounds 8-11:

8

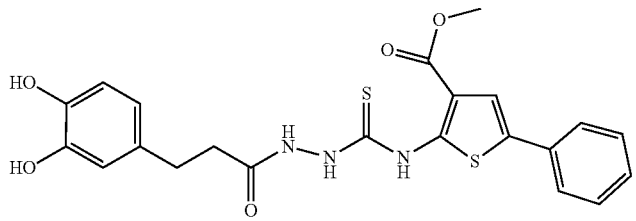

9

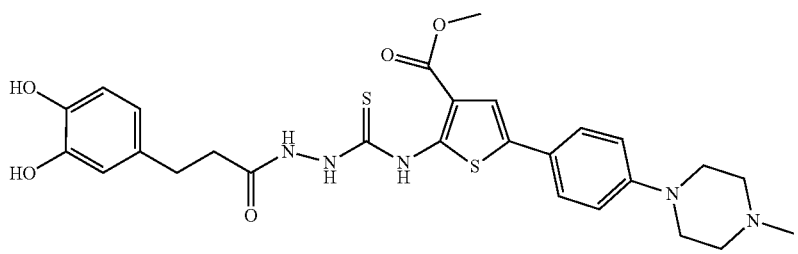

10

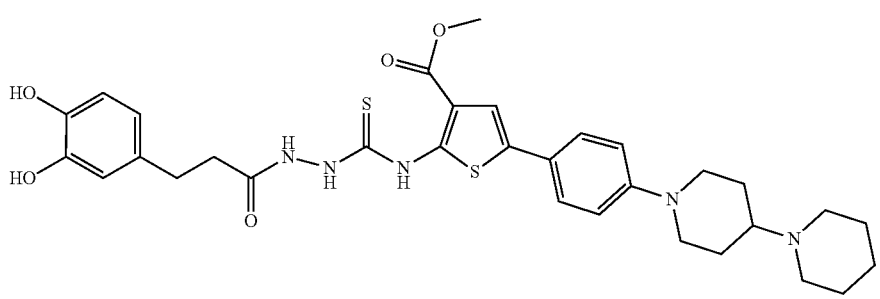

11

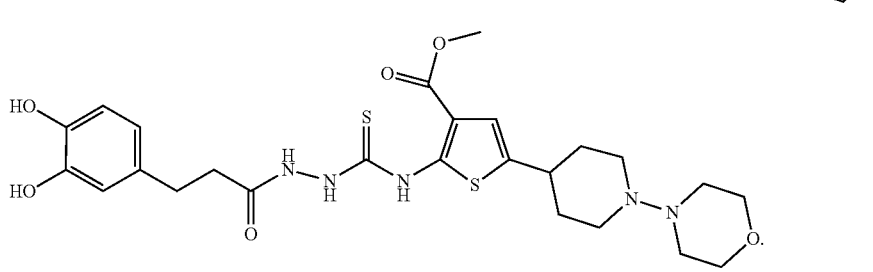

In another aspect, the present application provides a method for treating cancer, which comprises administering to a patient with cancer a therapeutically effective amount of zelpolib or a pharmaceutically acceptable salt thereof. The method encompasses administering zelpolib in combination with at least one additional chemotherapeutic agent.

Further, according to the present application, a method is provided for inhibiting cell growth comprising contacting a cell with zelpolib or a pharmaceutically acceptable salt thereof. In one aspect, the cell growth is inhibited in vitro. In a further aspect, the cell growth is inhibited in vivo.

In one or more embodiments, the methods according to the present application include providing zelpolib with a pharmaceutical excipient.

BRIEF DESCRIPTION OF THE DRAWING FIGURES

Figure 1C:
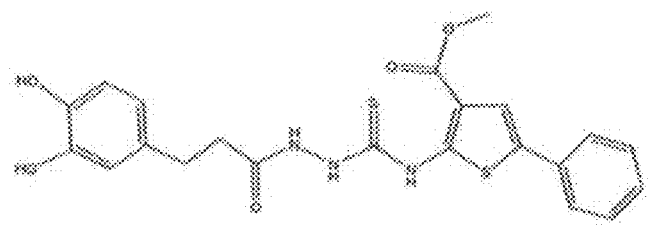
Figure 1B:
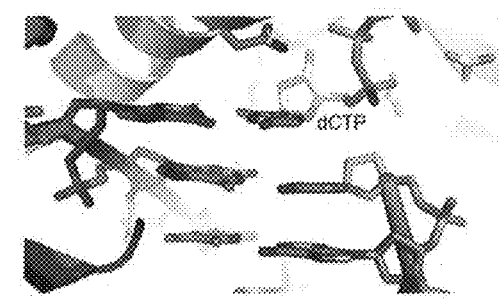
Figure 1D:
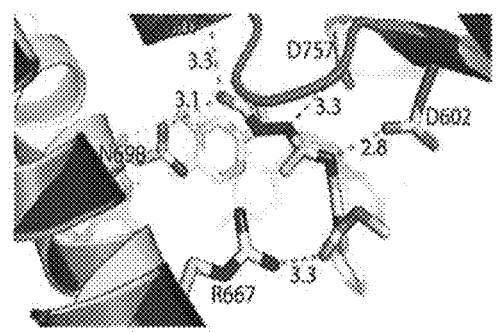

FIGS. 1A-1D. Interactions of Zelpolib at the active site of Pol δ in accordance with one or more embodiments. FIG. 1A, Zelpolib forms two hydrogen bonds with dG on the template strand. The catechol moiety stacks against dOC (dideoxycytosine) on the primer. FIG. 1B, comparative position of dCTP at the active site of Pol δ. FIG. 1C, chemical structure of zelpolib. FIG. 1D, 5 potential hydrogen-bonds can be formed between zelpolib and Pol δ.

Figure 2A:
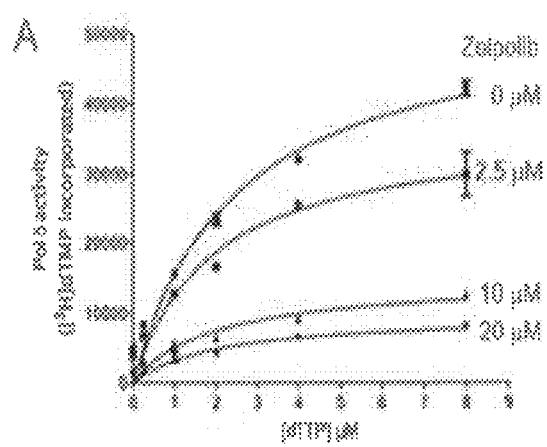
Figure 2C:
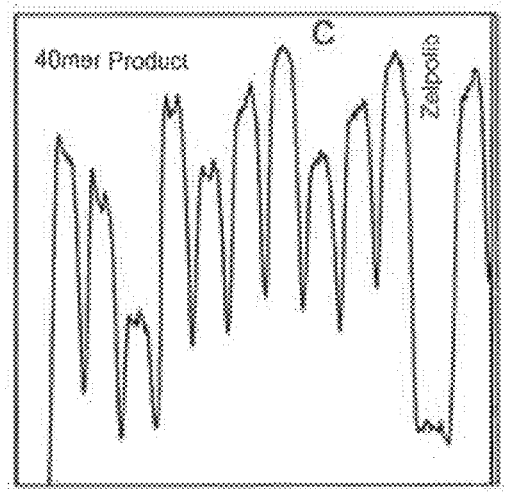
Figure 2B:
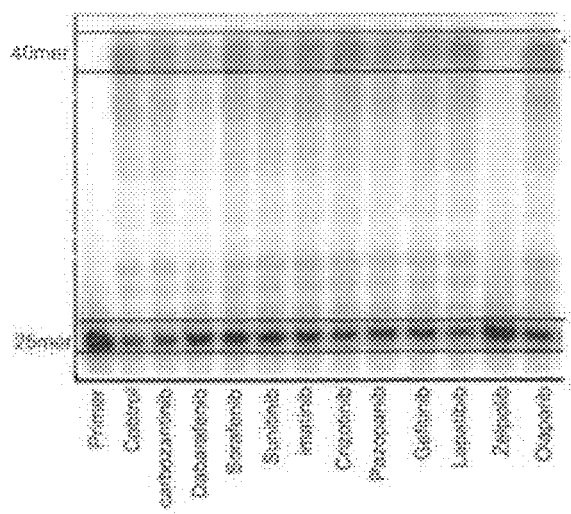
Figure 2D:
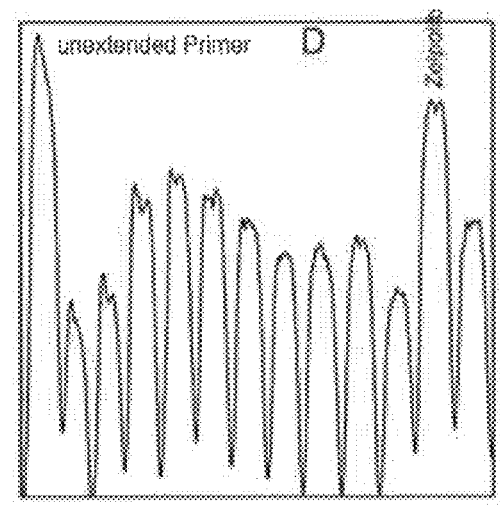

FIGS. 2A-2D. Zelpolib inhibits Pol δ activity in accordance with one or more embodiments. FIG. 2A, enzymatic assay by poly(dA)/oligo(dT) method demonstrates noncompetitive inhibition with $K_i$ of 4.3 μM. FIG. 2B, zelpolib is likely unique in inhibiting Pol δ activity among current FDA approved small molecule oncology drugs. FIG. 2C, quantification of the full-length products (40 mer, integration by ImageJ). Lower peak height indicates less products. FIG. 2D, quantification of unextended primer. Higher peaks correspond to higher amounts of primer left.

Figure 3A:
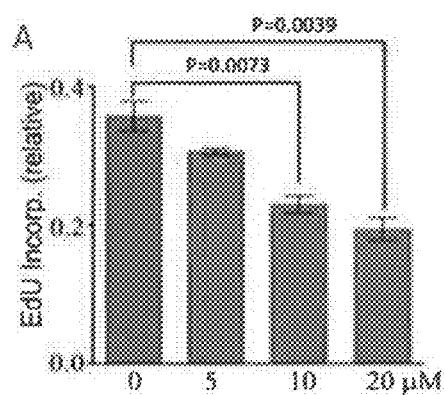
Figure 3B:
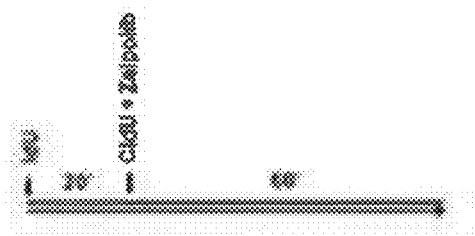
Figure 3D:
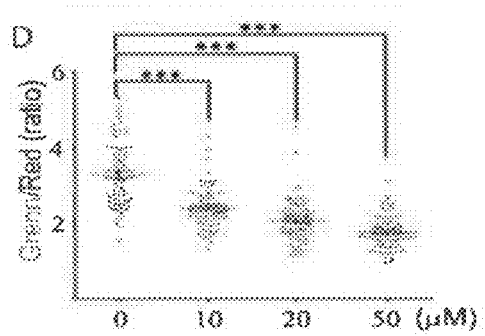
Figure 3C:
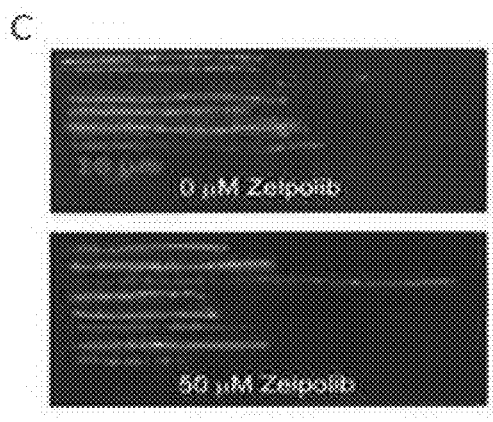
Figure 3E:
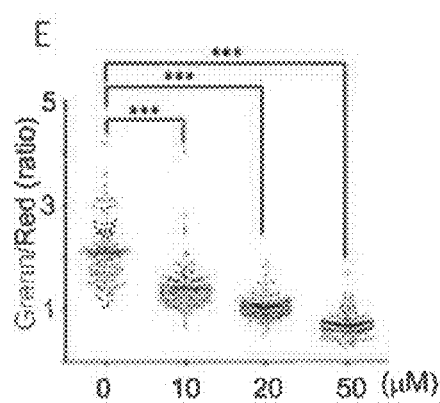

FIGS. 3A-3E. Zelpolib inhibits cellular DNA replication in accordance with one or more embodiments. FIG. 3A, EdU incorporation by whole cell population is inhibited by Zelpolib. Exponentially growing HCC1395 (TNBC) cells were treated with zelpolib for 2 hours prior to pulse labeling with EdU for 30 minutes. Amount of EdU quantified with "click"

chemistry and measured by laser scanning cytometry (LSC). Error bar shows mean value with SEM (triplicates) and P values were calculated using unpaired Stident T test. FIG. 3B, treatment scheme of DNA fiber flourography assay. FIG. 3C, DNA fiber-length comparison between untreated and treated with 50 µM zelpolib (HCC1395 cells, see FIG. 9 for original images). FIG. 3D, quantification of DNA fiber length for BxPC-3 cells. FIG. 3E, quantification of DNA fiber length for HCC1395 cells. 75 fibers were analyzed per sample. Scattered dot plot shows ratio of green/red fiber lengths (ratios) with SEM. P values were calculated using unpaired T test. *** indicates p<0.0001.

FIGS. 4A-4D. Antiproliferative activities of Zelpolib in accordance with one or more embodiments. Concentration dependent inhibition of cell proliferation by zelpolib on three different cell lines (FIGS. 4A-4C) by MTT assays. All samples were in triplicates and presented as averages with standard deviation. FIG. 4D, comparison with methotrexate, 5-FU and cisplatin in inhibition of BxPC-3 cell proliferation.

Figure 5A:
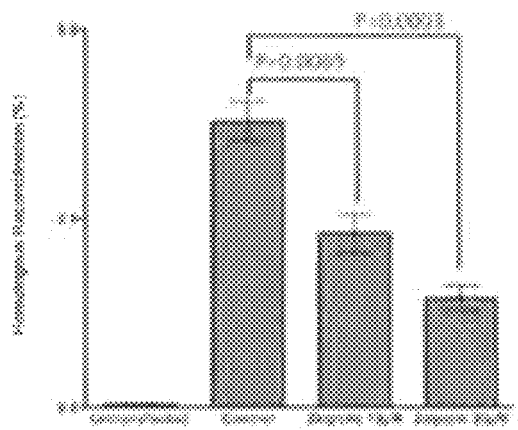
Figure 5B:
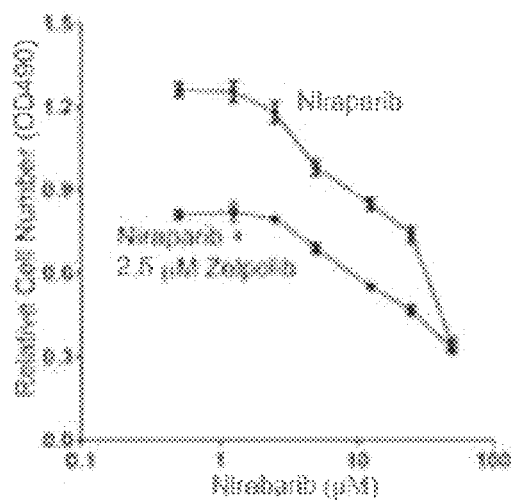
Figure 5C:
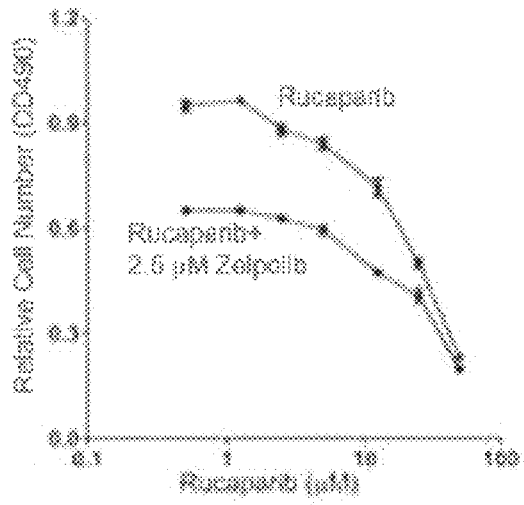
Figure 6A:
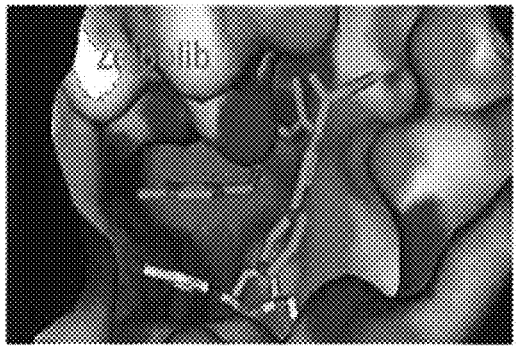
Figure 6C:
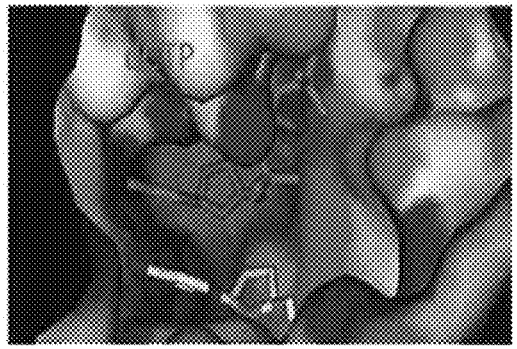
Figure 6B:
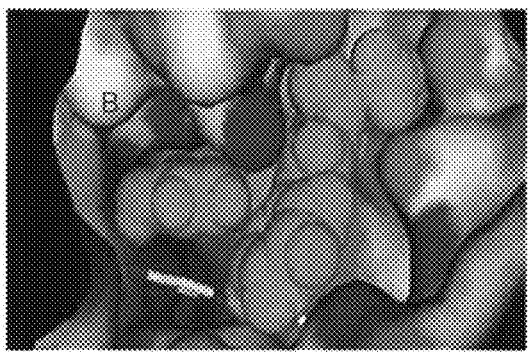
Figure 6D:
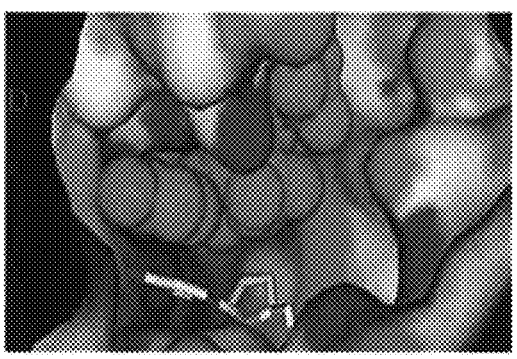

FIGS. 5A-5C. Zelpolib inhibits homologous recombination in cell-based assay in accordance with one or more embodiments. FIG. 5A, Dual plasmids (DR-GFP and I-Scel) reporter assay was used to measure the effect of Zelpolib on DSB repair in 293T cells as reported[34]. The error bar represents mean values of four repeats with SEM. P values were calculated using unpaired T test. FIG. 5B, Zelpolib enhances the sensitivity of triple negative breast cancer cells (HCC1395) to niraparib by MTT assay. FIG. 5C, Zelpolib enhanced the sensitivity of TNB cells (HCC1395) towards Rucaparib.

FIGS. 6A-6D. Comparison of Zelpolib with dCTP in binding to the active site of Pol δ in accordance with one or more embodiments. Zelpolib in stick (FIG. 6A) and ball (FIG. 6B) representation with dCTP (FIG. 6C and FIG. 6D) in comparison.

FIGS. 7A-7B. Dose-dependent inhibition of Pol δ activities by zelpolib in a primer extension assay in accordance with one or more embodiments. FIG. 7A, primer extension products were separated by 20% polyacrylamide gels and visualized by phosphorimaging. FIG. 7B, the full-length products (40 mer) were quantified with ImageJ.

Figure 8:
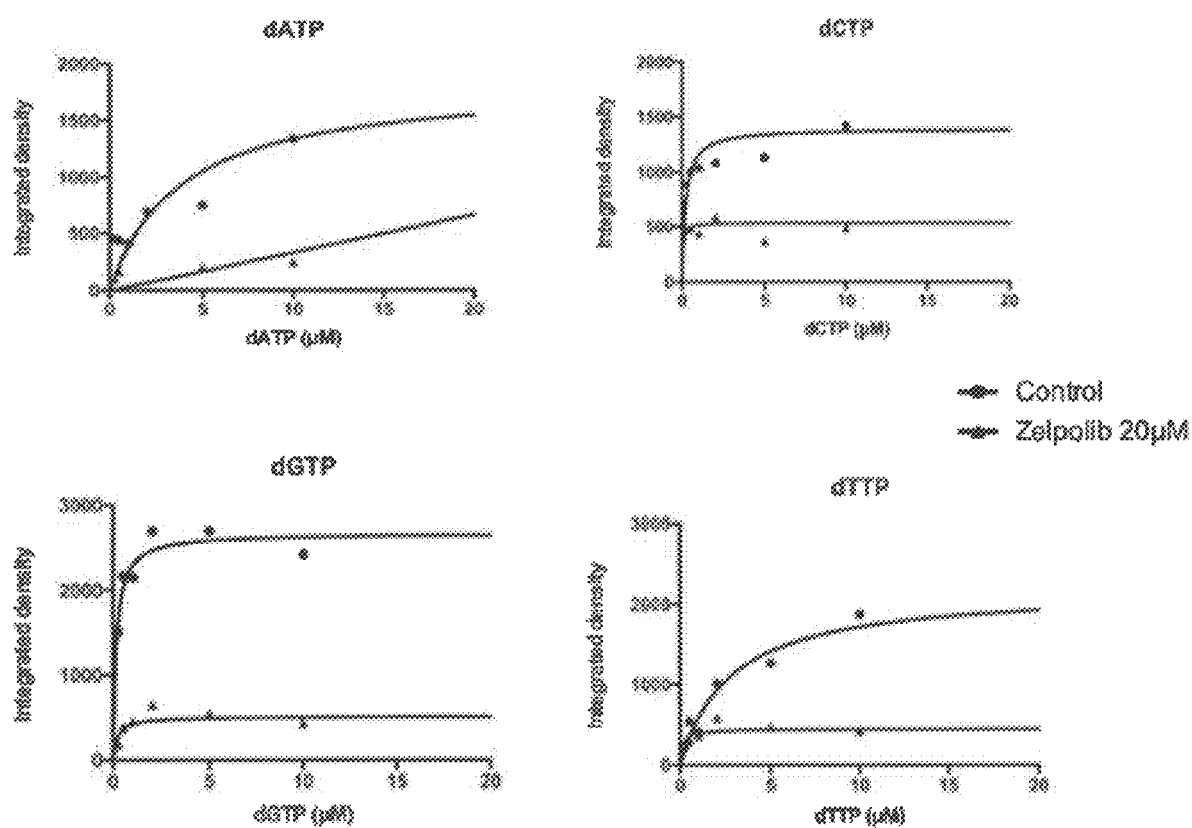

FIG. 8. Zelpolib inhibits the incorporation of all the four dNTPs in a noncompetitive manner in accordance with one or more embodiments. Zelpolib inhibits Pol δ catalyzed single nucleotide primer extension for dATP, dGTP, dCTP and dTTP.

FIG. 9. Unaltered image of DNA fiber presented in FIGS. 3A-3D in accordance with one or more embodiments. All eligible fibers were picked from these two images and aligned to produce FIG. 3C.

Figure 10A:
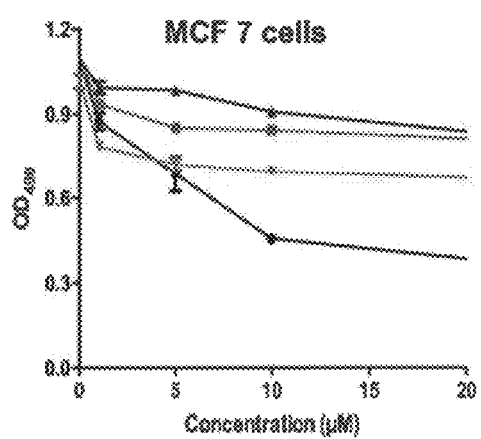
Figure 10B:
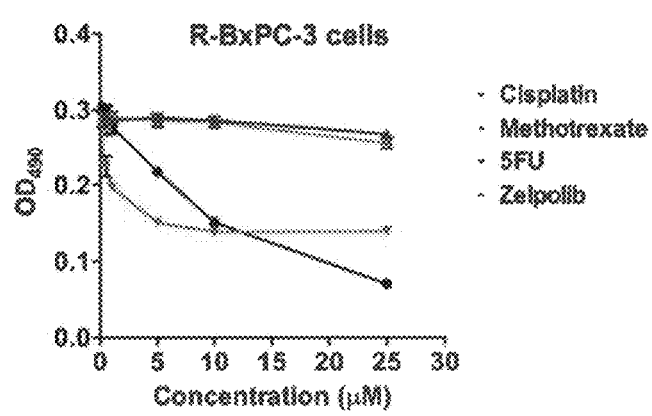

FIGS. 10A-10B. Comparison of antiproliferative properties of Zelpolib with current chemotherapeutic agents in accordance with one or more embodiments. FIG. 10A, MCF 7 cell viability was measured after 72 h treatment with zelpolib, cisplatin, methotrexate or 5-FU. All samples were in triplicates and cell viability was measured by MTT assay. Error bars represent the SEM. FIG. 10B, the viabilities of R-BxPC-3 cells were analyzed in identical protocol as in (FIG. 10A).

Figure 11:
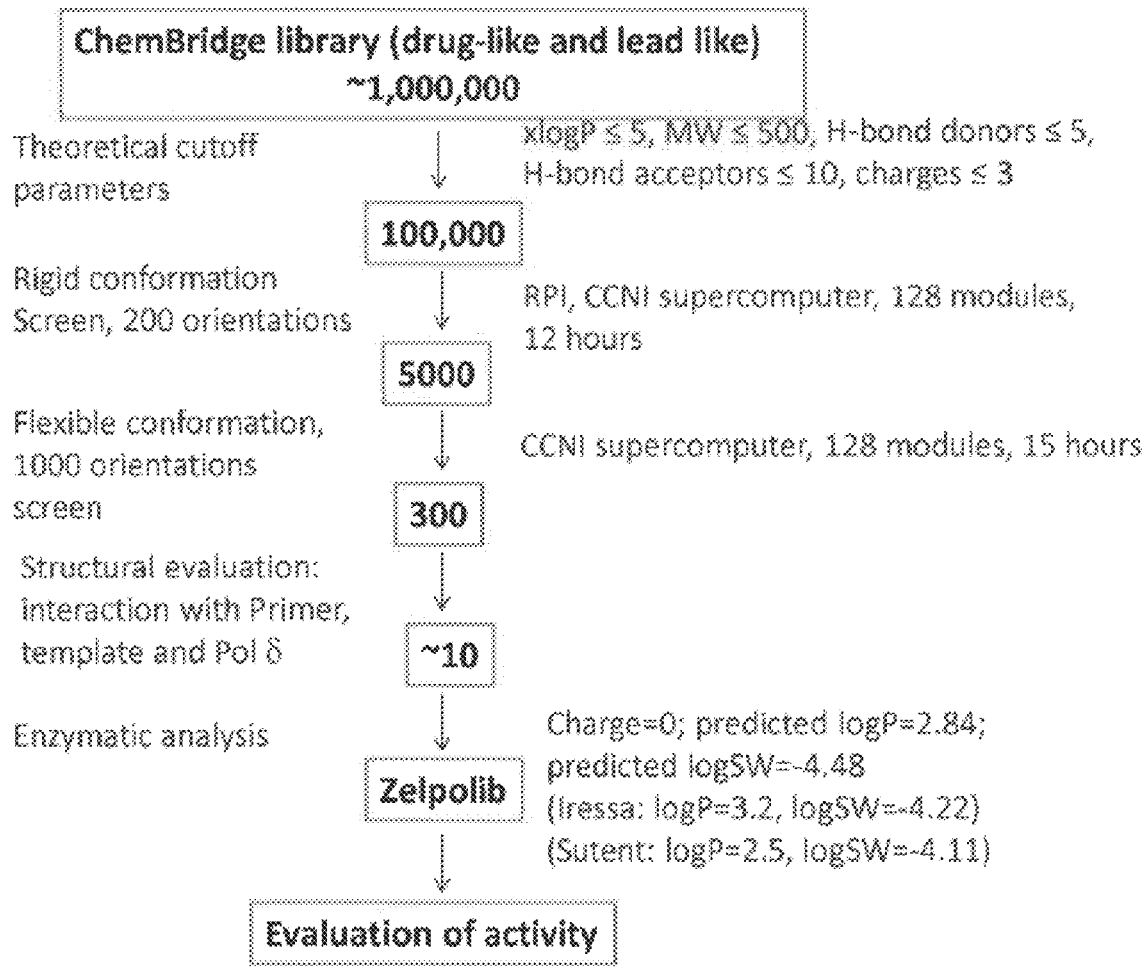

FIG. 11. Flow-chart of the in silico screening protocol by Dock6.4 of the ChemoBridge library in accordance with one or more embodiments.

Figure 12:
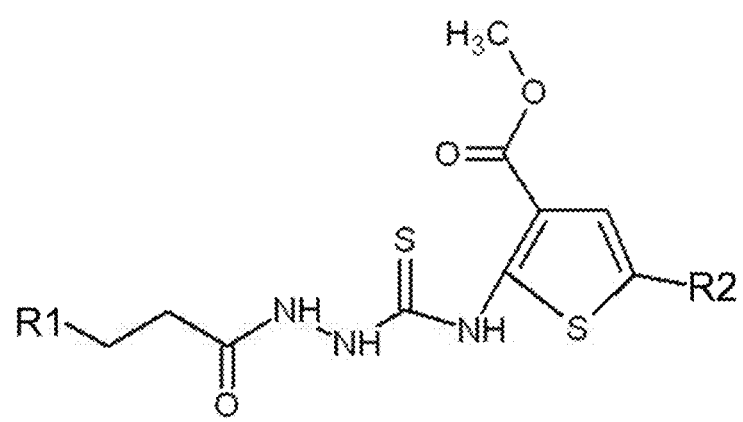

FIG. 12. A structural fold of inhibitors of DNA polymerase δ in accordance with one or more embodiments. R1 represent chemical moieties that can form hydrogen bond(s) with nucleotide bases that include adenine, thymine, guanine, and cytosine. R2 represents chemical moieties with molecular weight less than 200 Da that include but not limited to phenyl group.

Figure 13:
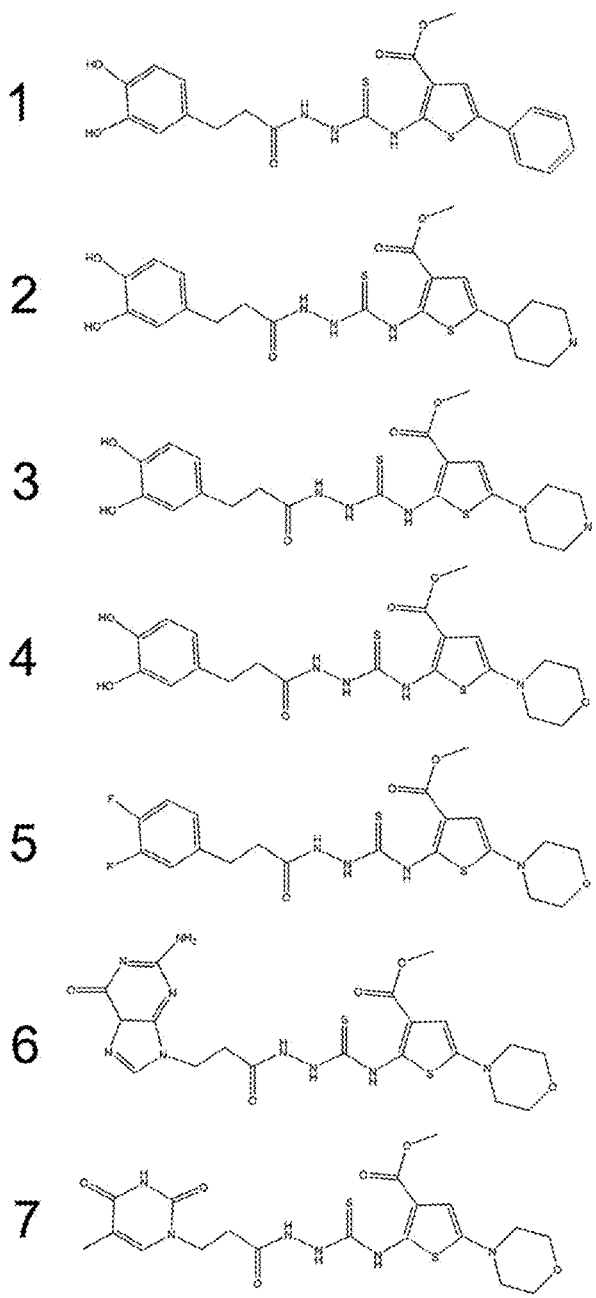

FIG. 13. Derivatives of parental fold of FIG. 12 (molecules 1-7) in accordance with one or more embodiments.

Figure 14:
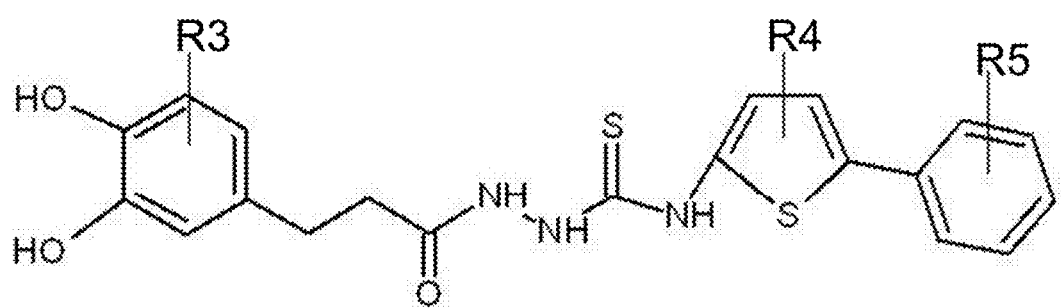

FIG. 14. Derivatives of zelpolib in accordance with one or more embodiments. R3, R4, and R5 represent derivatives of one or two substitutions of hydrogens with but not limited to fluoro, chloro, bromo, nitro, and sulfo.

Figure 15:
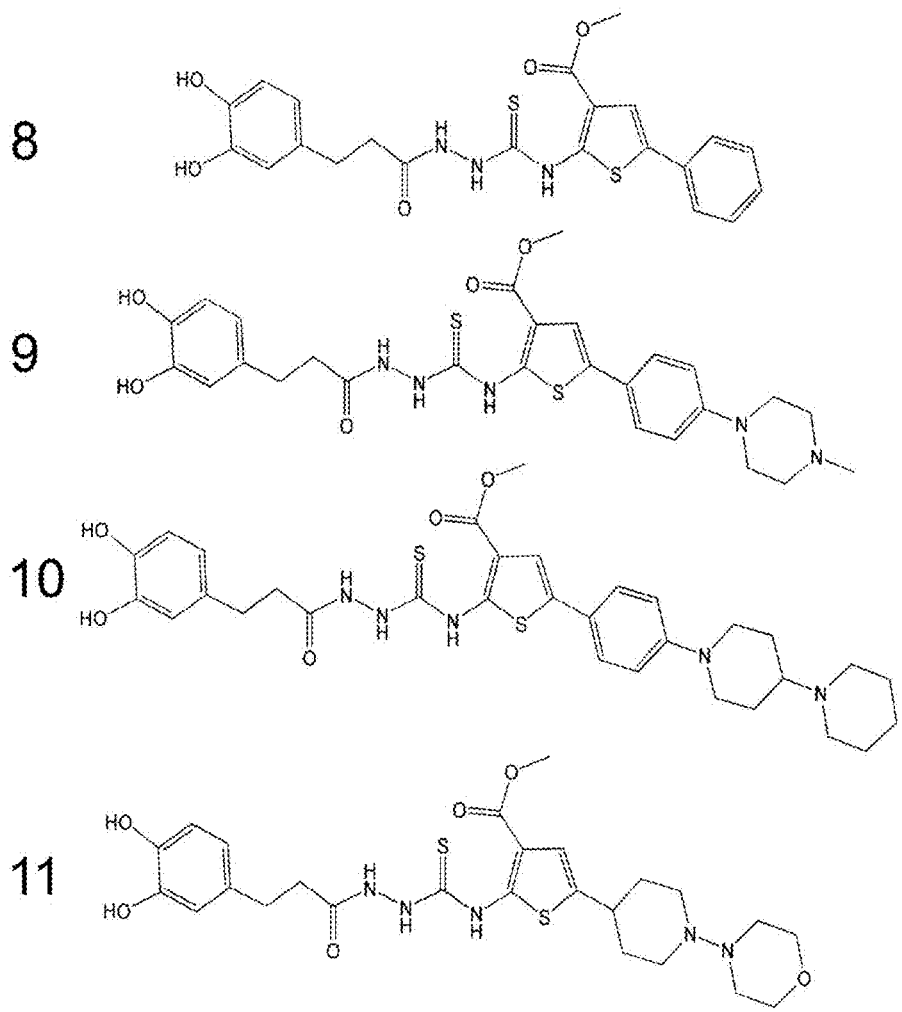

FIG. 15. Derivatives of zelpolib (compounds 8-11) in accordance with one or more embodiments.

DETAILED DESCRIPTION OF CERTAIN EMBODIMENTS IN ACCORDANCE WITH THE DISCLOSURE

By way of overview and introduction, the present application discloses methods and compounds for inhibiting cell growth, methods and compounds for inhibiting DNA polymerase activity, and methods and compounds for inhibiting DNA replication and repair. In one or more embodiments, the compounds are zelpolib, derivatives of zelpolib, or pharmaceutically acceptable salts of zelpolib.

There are three essential replicative DNA polymerases, Pol α, Pol δ and Pol ε. Cells will not replicate DNA without one of the three and inhibiting one is sufficient to disable chromosome duplication and cancer cell proliferation. On the other hand, the three replicative Pols share a common fold and near identical active site structures as shown by x-ray crystallography[12-14]. Inhibitors that bind to the active sites most likely will inhibit all three Pols simultaneously. U.S. Pat. No. 4,011,333 describes substituted thiophenecarboxylic acids as hypolipidemic agents. U.S. Pat. No. 3,507,874 describes 3-thiophenecarboxylic acid hydrazides as antihelminthic and amoebicidal agents.

Here we report the discovery of a novel antiproliferative agent, a Pol δ inhibitor zelpolib[15]. We show that zelpolib demonstrates robust inhibition of Pol δ in vitro and in vivo and exhibits superior antiproliferative activities to a number of current chemotherapeutic agents.

In one or more embodiments, a method of inhibiting cell growth is provided in which a cell, such as a cancer cell, is contacted with zelpolib or a derivative or pharmaceutically acceptable salt thereof. The cell growth can be inhibited in vivo, and in certain embodiments, the cell growth is inhibited in vitro.

In at least one embodiment, a method for inhibiting DNA polymerase activity is provided in which a DNA polymerase is contacted with zelpolib or a derivative or pharmaceutically acceptable salt thereof. In at least one embodiment, the DNA polymerase is Pol δ.

Moreover, in one or more embodiments, a method for inhibiting DNA replication and DNA repair is provided. For instance, in at least one embodiment of the method, a cell, such as a cancer cell, is contacted with zelpolib or a derivative or pharmaceutically acceptable salt thereof. The DNA replication and repair can be inhibited in vivo, and in certain embodiments, the DNA replication and repair is inhibited in vitro.

These and other aspects of the present methods and zelpolib compounds and are described in further detail below with reference to the accompany drawing figures, in which one or more illustrated embodiments and/or arrangements of the compounds and methods are shown. The compounds and methods of the present application are not limited in any way to the illustrated embodiment and/or arrangement. It should be understood that the compounds and methods as shown in the accompanying figures are merely exemplary of the compounds and methods of the present application, which can be embodied in various forms as appreciated by one skilled in the art. Therefore, it is to be understood that any structural and functional details disclosed herein are not to be interpreted as limiting the compounds and methods, but rather are provided as a representative embodiment and/or arrangement for teaching one skilled in the art one or more ways to implement the present compounds and methods.

Definitions:

As used herein, the terms "patient" or "subject" are used interchangeably and mean a mammal, including, but not limited to, a human or non-human mammal, such as a bovine, equine, canine, ovine, or feline. Preferably, the patient is a human.

As used herein, the phrases "treating cancer" and "treatment of cancer" and "treatment of tumors" mean to decrease, reduce, or inhibit the replication of cancer cells; decrease, reduce or inhibit the spread (formation of metastases) of cancer; decrease tumor size; decrease the number of tumors (i.e. reduce tumor burden); lessen or reduce the number of cancerous cells in the body; prevent recurrence of cancer after surgical removal or other anti-cancer therapies; or ameliorate or alleviate the symptoms of the disease caused by the cancer.

"Treating" or "treatment" of a state, disorder or condition includes:
(1) preventing or delaying the appearance of clinical symptoms of the state, disorder, or condition developing in a person who may be afflicted with or predisposed to the state, disorder or condition but does not yet experience or display clinical symptoms of the state, disorder or condition; or
(2) inhibiting the state, disorder or condition, i.e., arresting, reducing or delaying the development of the disease or a relapse thereof (in case of maintenance treatment) or at least one clinical symptom, sign, or test, thereof; or
(3) relieving the disease, i.e., causing regression of the state, disorder or condition or at least one of its clinical or sub-clinical symptoms or signs.

A "therapeutically effective amount" means the amount of a compound that, when administered to an animal for treating a state, disorder or condition, is sufficient to effect such treatment. The "therapeutically effective amount" will vary depending on the compound, the disease and its severity and the age, weight, physical condition and responsiveness of the animal to be treated.

Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

Combination treatment according to one or more embodiments of the present application includes administering zelpolib concurrently with, or separately from, other components in a treatment regimen. Additionally, the combination therapy described herein further comprises administering a chemotherapeutic agent, targeted therapy or radiation to the subject either prior to, simultaneously with, or after treatment with the combination therapy. The combination therapy described in the present disclosure can be used for the treatment of various types of cancers, including solid tumors. Non-limiting examples of cancers/tumors for treatment include melanoma (e.g., metastatic malignant melanoma), renal cancer (e.g. clear cell carcinoma), prostate cancer (e.g. hormone refractory prostate adenocarcinoma), pancreatic adenocarcinoma, breast cancer, colon cancer, lung cancer (e.g. non-small cell lung cancer), esophageal cancer, squamous cell carcinoma of the head and neck, liver cancer, ovarian cancer, cervical cancer, thyroid cancer, glioblastoma, glioma, leukemia, lymphoma, and other neoplastic malignancies. Additionally, the present disclosure includes refractory or recurrent malignancies whose growth may be inhibited using the combinations described herein.

Non-limiting examples of antitumor/chemotherapeutic agents include: paclitaxel, doxorubicin, daunorubicin, cyclophosphamide, methotrexate, 5-fluorouracil, thiotepa, busulfan, improsulfan, piposulfan, benzodopa, carboquone, meturedopa, uredopa, altretamine, triethylenemelamine, triethylenephosphoramide, triethilenethiophosphoramide, trimethylolomelamine, bullatacin, bullatacinone, camptothecin, bryostatin, callystatin, cryptophycin 1, cryptophycin 8, dolastatin, duocarmycin, eleutherobin, pancratistatin, sarcodictyin, spongistatin, chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, calicheamicin, dynemicin, clodronate, esperamicin, aclacinomycin, actinomycin, authramycin, azaserine, bleomycin, cactinomycin, carabicin, carminomycin, carzinophilin, chromomycin, dactinomycin, detorbicin, 6-diazo-5-oxo-L-norleucine, adriamycin, epirubicin, esorubicin, idarubicin, marcellomycin, mitomycin C, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin, denopterin, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone, aminoglutethimide, mitotane, trilostane, frolinic acid, aceglatone, aldophosphamide glycoside, aminolevulinic acid, eniluracil, amsacrine, bestrabucil, bisantrene, edatraxate, defofamine, demecolcine, diaziquone, elfornithine, elliptinium acetate, epothilone, etoglucid, lentinan, lonidamine, maytansine, ansamitocine, mitoguazone, mitoxantrone, mopidanmol, nitraerine, pentostatin, phenamet, pirarubicin, losoxantrone, podophyllinic acid, 2-ethylhydrazide, procarbazine, razoxane, rhizoxin, schizophyllan, spirogermanium, tenuazonic acid, triaziquone, roridine A, anguidine, urethane, vindesine, dacarbazine, mannomustine, mitobronitol, mitolactol, pipobroman, gacytosine, docetaxel, chlorambucil, gemcitabine, 6-thioguanine, mercaptopurine, cisplatin, oxaliplatin, carboplatin, vinblastine, etoposide, ifosfamide, mitoxantrone, vincristine, vinorelbine, novantrone, teniposide, edatrexate, daunomycin, aminopterin, xeloda, ibandronate, irinotecan, topoisomerase inhibitor, difluoromethylornithine (DMFO), retinoic acid, capecitabine, and pharmacologically acceptable salts or derivatives thereof.

Zelpolib can be administered to a patient by various routes including, for example, orally or parenterally, such as intravenously, intramuscularly, subcutaneously, intraorbitally, intracapsularly, intraperitoneally, intrarectally, intracisternally, intratumorally, intravasally, intradermally or by passive or facilitated absorption through the skin using, for example, a skin patch or transdermal iontophoresis, respectively.

Zelpolib can also be administered to the site of a pathologic condition, for example, intravenously or intra-arterially into a blood vessel supplying a tumor.

The following examples show, for example, the inhibition of cell growth, the inhibition of DNA polymerase activity, and the inhibition DNA replication and repair with zelpolib compounds.

Results

Identification of Zelpolib Through In Silico Screen.

Through two cycles of screening, top 300 compounds were selected for detailed analysis by PyMol. We aimed to select compounds that will inhibit Pol δ when it is actively engaged in DNA replication. We selected 10 compounds that satisfy our requirements. At the minimum, three key requirements are necessary: interaction with template strand, hydrophobic stacking with the preceding nucleotide base of the primer, and extensive interaction with Pol δ. All selected compounds showed inhibition of Pol □ activity when assayed at 100 µM with the poly(dA)/oligo(dT) assay (data not shown) and only one compound which showed significant inhibition when assayed at 10 µM. This compound, subsequently named Zelpolib (FIG. 1C, Zilch Polymerase activity), also predicted to have reasonable pharmacological properties. Zelpolib exhibited a unique binding mode in the model structure (FIG. 1A). The catechol moiety occupies the base position of the incoming nucleotide (FIGS. 1A and 1B), in a position to form hydrophobic stacking with previous base of the primer (cytosine). The catechol groups are in position to form two hydrogen bonds with guanine on the template strand (FIG. 1A). In fact, half of the inhibitor molecule (from catechol to thiourea segment of the inhibitor, FIG. 1C) almost overlaps with the incoming nucleotide in the crystal structure (3IAY.PDB, dCTP, FIG. 1A vs 1B). In the final refinement model, zelpolib is also in position to form 5 potential hydrogen bonds with Pol δ (FIG. 1D). The three residues forming hydrogen bonds with zelpolib, N698, D602 and D757, also play important roles in interaction with incoming nucleotide (3IAY). Potentially, more hydrogen bonds are formed between amide of Y607 and guanidine side chain of R667 with Zelpolib. Overall, zelpolib occupies significantly more space within the Pol δ active site (Supplemental FIGS. 6A-6D) than the incoming nucleotide and is projected to be a strong inhibitor that binds to Pol δ active site when it is in complex with template/primer, i.e., when actively synthesizing DNA during replication or repair.

Inhibition of Pol δ Activity by Zelpolib in Enzymatic Assays

In order to validate the predicted inhibitory properties of zelpolib, we used the well-established DNA polymerase assay, poly(dA)/oligo(dT) method[1,16], to quantify the inhibition constants. In this assay, a poly(dA) template (up to 4 kilobases) was randomly primed with oligo(dT) primers (40 mer). In the presence of proliferating cell nuclear antigen (PCNA), Pol δ will initiate the elongation of oligo dT primer with the incorporation of radio-labeled deoxythymidine ($^3$H). The polymerase activity can then be precisely quantified by counting the isotope incorporated. In this assay, zelpolib showed robust inhibition of Pol δ activity in a non-competitive manner (FIG. 2A) against dTTP with an inhibition constant $k_i$ of 4.3±0.3 µM ($R^2$=0.99).

Next, we investigated the inhibitory properties of zelpolib in a primer extension assay[17,18] with a template that consists of all four deoxynucleotide that is more reflective of cellular DNA replication processes than the polD(A) template. The substrate consisted of a 25 mer primer hybridized to a 40 mer template. In the presence of PCNA and dNTPs, the primers were extended upon addition of Pol δ and a full extension would generate a 40 mer copy of the template. The primers were labeled at the 5'-end with $^{32}$P, and the products were separated on a sequencing gel for visualization and quantification. Consistent with results from poly(dA)/oligo (dT) assays, zelpolib showed concentration dependent inhibition of the primer extension activities of Pol δ (Supplemental FIGS. 7A-7B). In the second assay, we aimed to investigate whether inhibition of DNA replication is exhibited by other existing cancer drugs, especially kinase inhibitors. The idea originated from the fact that most kinase inhibitors compete for binding with ATP. It is conceivable that they might compete with dATP for binding to polymerases. We randomly selected 10 small-molecule-cancer drugs with nine being kinase inhibitors[19] and one parp inhibitor (olaparib)[20]. At 20 µM, zelpolib was the only molecule shown to exhibit robust inhibition of Pol δ activity (FIG. 2B), with 94% of the primer unextended (FIG. 2D). In the presence of any other inhibitors, at least 30% of the primers were extended. If we analyze the full-length product formed, it is barely detectible in the presence of 20 µM zelpolib, whereas in the presence of any other inhibitors, the full-length products are clearly detectible (FIG. 2C).

In our in silico screening, the active site cavity was created by the removal of dCTP in the original crystal structure. One of the questions we asked was if zelpolib displays any preference in the inhibition of a specific dNTP among the four dNTPs. Therefore, we assayed the inhibition patterns of 4 individual dNTP molecules in a single nucleotide incorporation assays. In this assay, only one nucleotide is present for the primer extension for the next appropriate base paring to the template. Interestingly, zelpolib inhibited the incorporation of all four nucleotides to similar extents in a noncompetitive manner (FIG. 8).

Our enzymatic analysis of zelpolib on Pol δ activity validated the in silico screen results. Zelpolib showed strong inhibition of Pol δ activity in two different assays and inhibited the incorporation of all four nucleotide in an uncompetitive manner with $K_i$ in the µM range. In addition, the mechanism of inhibiting DNA replication by zelpolib is not likely shared by other small molecule drugs currently in clinical application in oncology.

Zelpolib Inhibits DNA Replication Directly Under Cellular Conditions.

Upon establishing that zelpolib inhibits Pol δ activities in enzymatic assays, we conducted experiments to establish that zelpolib inhibits DNA synthesis in vivo. Extensive cellular studies have shown that kinase inhibitors can arrest cell cycle progression and induce apoptosis[21] upon prolonged exposure of 24 to 96 hours. The effects of prolonged exposure may be a combination of many cellular pathway disturbances that eventually results in halting DNA synthesis. In order to assess the direct effect on DNA replication, we avoided any prolonged cellular exposure to zelpolib so that any effects on DNA replication are not due to cell cycle regulation. On our first assay, we incubated cells with zelpolib for 1 to 2 hours to ensure uptake. Then the cells were pulse labeled with 5-ethynyl-2'-deoxyuridine (EdU)[22] so that the majority of incorporation was due to ongoing DNA replication processes. The uridine analog, EdU, is incorporated into DNA as dTTP analogs and can be detected by "Click" chemistry with fluorescent azide[22,23]. We tested zelpolib on a pancreatic cancer cell line, BxPC-3 cells, followed by EdU incorporation analysis using laser scanning cytometry. Zelpolib showed concentration dependent inhibition of EdU incorporation. The integrated fluorescence signal is shown in FIG. 3A, with significant reduction of EdU incorporation at 10 and 20 µM in comparison with sham treatment.

In our search for Pol δ inhibitors, we focused on the identification of inhibitors that can inhibit Pol δ when it is actively replicating DNA. DNA fiber fluorography with dual labeling technique[24] provides a possibility that we can analyze the effect of zelpolib on ongoing DNA replication at a single molecule level. Both IdU and CldU are halogenated thymidine analogs that can be incorporated into DNA. Subsequent DNA fiber spreading and antibody detection are used to directly visualize the replicated DNA fiber. The incorporation of IdU gives rise to red fibers and CldU produces green fibers with subsequent antibody detection[24]. Therefore, in this assay, the cells were first incubated with IdU for 20 minutes in the absence of zelpolib (FIG. 3B) to establish ongoing DNA replication and the basal replication rates of each individual DNA fibers. Subsequently, CldU were added to cell culture either with or without simultaneous addition of zelpolib. DNA replication were allowed for an additional hour. For any ongoing replication, the green fiber (60 minutes of replication) should be collectively about 3 times the length of the red fiber (20 minutes of replication, FIG. 3B) either in the absence of zelpolib or even in the presence of zelpolib if the cells failed to take up zelpolib fast enough in that short duration. Under this stringent condition, zelpolib showed concentration dependent inhibition of ongoing cellular DNA replication (FIG. 3D, BxPC-3 cells). In order to be certain that this inhibition was not cell line dependent, we conducted an identical experiment on a triple-negative breast cancer cell line as well. All three concentrations of zelpolib showed significant inhibition of ongoing DNA replication (FIGS. 3C and 3E). The DNA fibers (FIG. 3C) from a single field of view (FIG. 9) were realigned for visual comparison.

These cellular studies demonstrated that zelpolib inhibits cellular DNA replication significantly with concentrations that inhibited Pol δ activities in enzymatic assays. The DNA fiber analysis also demonstrates that, as intended in the screening protocol, zelpolib can be taken up readily by cancer cells and inhibits ongoing DNA replication. At 20 µM, zelpolib inhibited the DNA fiber extension by about 40%, indicating that cellular uptake took less than 30 minutes as the total exposure time was 60 minutes.

Zelpolib Displayed Superior Antiproliferative Properties to a Number of Widely Used Anti-Cancer Drugs.

DNA replication precedes cell division. Thus, cancer cells cannot divide and proliferate without successful chromosomal duplication. A DNA polymerase inhibitor should inhibit cancer cell proliferation. We characterized the antiproliferative properties of zelpolib on a number of cell lines originated from pancreatic cancer (BxPC-3) and breast cancer (MCF7 for ER+ breast cancer). In addition, we developed a cisplatin resistant subline of a pancreatic cancer cell line, R-BxPC3 for our studies as well. We used the MTT method[25] for analyzing cell proliferation. This assay is based on the reduction of 3-(4,5-dimethylthiazol-2-yl)-2,5-diphenyltetrazolium bromide by live cells to an insoluble formazon, which were subsequently dissolved in DMSO and quantified by UV absorbance. Therefore, the cell number is proportional to the optical density in the established linear region. Based on this assay, zelpolib showed robust antiproliferative properties against BxPC-3, R-BxPC-3, and MCF7 cells (FIGS. 4A, 4B, 4C), all reaching a plateau at about 5 µM. The plateau phenomena indicate inhibition of proliferation without cell killing, similar to these observed from hydroxyurea[26], aphidicolin[27], and to a certain extent, methotrexate treatments[28]. Direct inhibition of DNA polymerase activity provides a unique mechanism that is not employed by any of the current cancer therapeutics. We selected a number of most widely prescribed chemotherapeutics with distinct mechanisms to compare their antiproliferative potential in the 2 cancer cell lines. We included alkylating agent cisplatin, antimetabolites methotrexate and 5-flourouracil (5FU)[29-31]. When investigated on pancreatic cancer BxPC-3 cells, zelpolib is superior to methotrexate and 5-FU at all concentrations; is superior to cisplatin up to 10 µM (FIG. 4D). With MCF7 cells, zelpolib is superior to methotrexate and 5-FU across the concentration range. Whereas the comparison with cisplatin is biphasic. Zelpolib is at least as effective as cisplatin in inhibiting MCF7 cell growth up to 5 µM, whereas cisplatin is more effective beyond 5 µM, as the cytotoxic effects of cisplatin start to dominate (FIG. 10A). Similar advantages of zelpolib were also observed with cisplatin-resistant Pancreatic cancer cells (FIG. 10B, R-BXPC-3).

Indeed, zelpolib provides effective antiproliferative activities with a unique mechanism of action, which has not been successfully employed in current cancer therapeutics.

Zelpolib Inhibits DNA Double Strand Break Repair by Homologous Recombination (HR).

In addition to being indispensable for the duplication of chromosomes, Pol δ also plays critical roles in various DNA repair pathways[32]. It has been shown that Pol δ is the preferred polymerase for the D-loop extension during homologous recombination repair[33]. Thus, we investigated the effect of zelpolib on HR efficiency. We used the two plasmid DR-GFP assay developed by Nakanishi et al[34], which is a modified version of the initial method[35]. The first plasmid contains a mutant GFP that has lost the ability to fluoresce. The second plasmid contains the coding region of a restriction enzyme, I-SceI. The co-transfection of the two plasmids will result in the expression of I-SceI, which can digest the DR-GFP plasmid at the mutation site leading to the formation of a double strand break. Successful homologous recombination repair of the double strand break will restore the GFP fluorescent signal. Therefore, the percentage of fluorescent cells is the readout of the efficacy of HR. In order to have conditions for valid comparison, HEK 293T cells were transfected with both plasmids under identical conditions. The transfected cells were allowed to recover for 4 to 5 hours and then replaced with fresh media. Subsequently, zelpolib were added at two different concentrations. The efficacy of HR was analyzed about 40 hours later by flow cytometry. Zelpolib showed dose-dependent inhibition of HR (FIG. 5A). The reduction in HR efficacy at 20 µM zelpolib is comparable to those induced by siRNA knockdown of BRCA1 or BRCA2 individually as reported[36].

Zelpolib Increases the Sensitivity of HR Proficient Cells to PARP Inhibitors.

PARP inhibitors have been a breakthrough therapy for HR-deficient ovarian cancers due to BRCA1/2 mutations[37-41]. However, there have been minimal clinical benefits for HR-proficient cancers[37-41]. Since zelpolib can inhibit HR, we explored the effect of zelpolib in combination with PARP inhibitors on HR-proficient cancer cells. The hypothesis is that zelpolib will lead to an HR-defect through inhibition of Pol δ and render HR-proficient cells sensitive to PARP inhibition. We tested the combination on a triple-negative breast cancer cell line, HCC1395, which is insensitive to PARP inhibitors Niraparib[42] or Rucaparib[43]. The cells were treated with increasing concentrations of PARP inhibitor Niraparib (FIG. 5B) or Rucaparib (FIG. 5C) in the absence or presence of 2.5 µM zelpolib for 48 hrs. The number of cells were then analyzed by MTT assay. Zelpolib increased the sensitivity of HCC1395 cells to Niraparib across the whole range of concentrations, with the differences being significant up to 20 μM. The effect of 25 μM of Niraparib on the proliferation of HCC1395 cells can be achieved by 5 μM in the presence of 2.5 μM zelpolib. The combination of zelpolib with Rucaparib behaved similarly to zelpolib and Niraparib combination, with the difference being statistically significant up to 25 μM.

Inhibition of the polymerase activity required for homologous recombination by zelpolib can render HR proficient cells more sensitive to PARP inhibition.

Discussion

Advantages of a Reversible Polymerase Inhibitor

Current cancer therapies take advantage of the quantitative differences in biological pathways between cancer and non-cancer cells. These differences have been summarized by the landmark publication of "Hallmarks of Cancer"[44] by Hanahan and Weinberg and a subsequent update[45]. Among these, the most prominent difference is the rate of proliferation. The high proliferating rates of cancer cells demand expedited nutritional supply through accelerated neoangiogenesis, and rapid chromosome duplication at the sacrifice of genomic stability through inactivation of checkpoint and DNA repair pathways. In fact, these differences and vulnerabilities have been the targets of the majority of current therapeutic regimen. Kinase inhibitors, especially VEGFR inhibitors, disrupt neoangiogenesis[46,47] and inhibit cancer cell proliferation. These inhibitors are an essential part of our current anticancer arsenal.

On the disruption of chromosome duplication front, the most successful chemotherapy reagents target DNA replication by direct DNA damage. These drugs include platinum derivatives that form DNA interstrand crosslinks, and alkylating agents that modify DNA bases. These reagents can modify DNA of all cell types and impact normal cellular function on many fronts. One of the unintended consequences of direct DNA damage is the effect on gene transcription inhibition[10,48], a necessary cellular activity shared by all cells, proliferating or quiescent. Some of the side effects and toxicities of DNA damaging agents likely originate from inhibition of transcription in normal tissues[49]. The consequences of transcription inhibition are somewhat under-appreciated, even though the toxicity from α-amanitin, the toxin from some poisonous mushrooms, is well known[50,51]. The initial effects of α-amanitin exposure share significant similarities with those from chemotherapy, such as abdominal pain, vomiting, and diarrhea[51,52]. Evidently, for cancer treatment, the challenge is to inhibit DNA replication with minimal impact on other nucleotide metabolism pathways such as transcription.

A reversible inhibitor of replicative DNA polymerases is one of the candidates that may accomplish the goal of inhibiting DNA replication without significant impact on other cellular processes such as transcription or translation. This is partially confirmed by results from this study, as zelpolib alone showed minimal cell cytotoxicity with pronounced antiproliferative activities. Additional support is from studies on one of the well-characterized replicative polymerase inhibitor, aphidicolin. A number of publications have shown the robust anticancer activities of aphidicolin in cell line and animal models[53-56]. More importantly, the safety profile in mice[55] and phase 1 clinical study[57] further validated the tolerability of polymerase inhibitors. However, aphidicolin progressed no further in clinical development due to limitations in biological availability and stability[55,57].

Inhibition of cellular polymerases requires much lower concentrations of inhibitors in comparison with tyrosine kinase inhibitors, if the inhibition constants were comparable. There are over 30 kinase inhibitors which have been widely used to treat various cancers. The difficulty in inhibiting kinases arises from the fact that cellular ATP concentrations are relatively high (2-10 mM) and its $K_m$ values of ATP towards kinases are generally in the 10 to 50 μM range. Therefore, it requires a high [inhibitor]/$K_i$ ratio for the inhibitors to overcome the ATP saturation of kinase active sites. On the other hand, the deoxyribonucleotide concentrations (dNTPs) are much lower and generally in the micromolar range[58,59], therefore it requires lower inhibitor [inhibitor]/$K_i$ ratio to compete with dNTPs for the polymerase active sites. These analyses are supported by the fact that nucleoside analogs such as cytosine arabinoside[60,61] (ara-C), which has similar affinities towards polymerases after conversion to triphosphate to those of dNTPs, is effective in cancer therapy.

The antiproliferative potential and unique mechanism of action zelpolib displays can make it a component of cancer therapy to minimize toxicities of current cancer chemotherapeutics.

Inhibition of DNA Repair

The majority of current cancer therapeutics has been based on the quantitative differences in biochemical pathways between cancer and non-cancer cells. More recent advances take advantage of the qualitative differences between cancer and non-cancer cells to minimize the side effects or to induce more durable responses. The breakthroughs come from investigations on the deficiencies in cancer cells, notably DNA repair pathways[62]. The universally increased genomic instability of cancers most likely originates from loss of certain DNA repair functions, some have been identified and others remain to be characterized. Two identified pathways, homologous repair deficiency and mismatch repair defect, have been characterized across many cancer types, with HR deficiency due to BRCA1/2 mutations mainly in female reproductive cancers[63] and MMR deficiency[64] in colorectal cancers[65].

The first major advance in a long time in ovarian cancer treatment come from the discovery that nearly half of epithelial ovarian cancers (EOCs) are HR deficient due to genetic and epigenetic alterations and roughly 40 percent of these are due to BRCA1/2 mutations[66]. Cancers with HR defects have exquisite sensitivity to PARP inhibition as a consequence of synthetic lethality. In 2012, results from a pivotal clinical trial with olaparib for the maintenance therapy in patients with platinum-sensitive relapsed disease attained a hazard ratio of 0.18[20] (82% reduction in the risk of progression or death) in progression-free survival for the BRCA1/2 mutant population. Subsequent clinical trials with other PARP inhibitors, niraparib[67] and rucaparib[43], showed similar efficacy to olaparib[38]. These results are unprecedented, considering the challenges throughout the years in treating ovarian cancers. In addition, PARP inhibitors have been well tolerated and patients have been on olaparib continuously for many years under maintenance settings.

The loss of MMR function, which results in microsatellite instability[65] (MSI), was first observed in colorectal cancer. Later, it was found in a small percentage of cancers of all types. Clinical trials have shown that cancers with MSI, regardless of organ origin, respond favorably to immunotherapy with pembrolizumab, a monoclonal antibody that blocks PD-1 induced immune suppression[68,69]. Sensitivity to immunotherapy represents a breakthrough in cancer therapy, as these responses are generally durable and significantly prolong patient survival.

However, both breakthrough treatments are limited by the facts that only a small percentage of all cancers have either HR or MMR defects. The question is whether these defects can be induced to cancers without genetic mutations in HR or MMR proteins. Both HR and MMR pathways involve many proteins that coordinate the repair process, and may provide targets for pharmaceutical interventions. One common enzymatic activity required for both pathways is DNA polymerization, through a polymerase. In HR, the required DNA polymerase has been suggested to be either Pol δ or Pol ε, with reported preference for Pol δ[33]. SiRNA knockdown of either protein reduces the HR efficacy by about 50%. Other polymerases, such as Pol □ and Pol □, have been implicated by a limited number of publications[70]. In MMR, a polymerase is required to refill the gap post excision and most studies suggest the role is filled by Pol □[71].

Zelpolib, a Pol δ inhibitor, displays robust inhibition of the homologous recombination process and renders HR proficient triple negative breast cancer cells more sensitive to PARP inhibition. These results suggest possible clinical applications to widen the scope of applicability of PARP inhibitors. More broadly, the participation of Pol δ in a wide range of DNA repair pathways imply that zelpolib will impact many DNA repair pathways in cancer cells. The disruption of these DNA repair pathways may render various cancers more responsive to advanced immune therapies available today and tomorrow.

Materials and Methods

In Silico Screening of Compound Library

A model structure of the catalytic domain of human Pol δ was generated based on the structure of yeast pol δ[72] by SWISSPDB[73]. The primary sequences of both proteins are conserved and the active sites structures were virtually identical between the model structure and that of yeast pol δ. The bound primer/template was kept in the complex whereas the incoming nucleotide was removed in order to identify molecules that occupy the active site. Residues within a radius of 10 Å of the ε-amino group of residue 694K were defined as the active site to construct a grid for the virtual screening. The compound library from ChemBridge (~1,000,000 compounds) from ZINC database was used for screening. Initial cutoff loosely based on Lipinski's Rule of Five[74] (x log P<5, MW<500, H-bond donors<5, H-bond acceptors<10, and charges<3) reduced the library size to 100,000. A three-step protocol (supplemental FIG. 11) was used with DOCK (6.4)[75] to complete the screening process. The most probable conformation of the compound was initially used as a rigid molecule and maximum orientation of 200 to was used in the first step. The 5,000 compounds with the highest scores were selected for a second cycle of screening. In this cycle, the conformations of these compounds were regarded as flexible and the maximum number of orientations was increased to 1,000. Subsequently, the 300 compounds with the highest scores were selected and analyzed by Pymol. The individual structural analysis with PyMol was to select compounds that may inhibit Pol δ when it is actively engaged in DNA replication. We set three key requirements for the selection process: 1) the compound can interact with the template strand, especially the nucleoside base that incoming nucleotide will pair with; 2) the compound can form meaningful hydrophobic interactions with the preceding nucleotide base of the primer, preferably through π-π electron interactions; 3) extensive interaction with Pol δ. 12 compounds satisfied our initial requirement and were purchased for initial enzymatic analysis by poly (dA)/oligo(dT) with inhibitor concentrations of 100 μM. Further assay with 10 μM concentration narrowed the choice to a single compound.

Cell Culture

MCF7, BxPC-3, HCC1395, and 293T cells were purchased from American Type Culture Collection (ATCC, Manassas, Va.) and maintained in media recommended by ATCC. Cisplatin resistant pancreatic cancer cell line, R-BxPC-3, was derived from parental BxPC-3 cells with sequential increases in the concentration of cisplatin with the final concentration of 1.25 μM according to protocol published previously[76,77].

Protein Expression and Purification.

Recombinant Pol μ were expressed in insect cells and purified as reported previously[18]. PCNA was expression in E. coli and purified as reported[18].

DNA Polymerase Assay.

Three different assays are used to analyze DNA polymerase activities and the impact of zelpolib. The poly(dA)/oligo(dT) assay[1,16] were used for precisely quantification as reported. Briefly, the standard reaction mixture for DNA polymerase assay contained 0.375 μM sparsely primed poly(dA)/oligo(dT) (Supertechs, MD), 150 μg/ml BSA, 7.5% glycerol, 7.5 mM MgCl2, 75 mM HEPES (pH 6.5), 0.75 μM [$^3$H]dTTP (100 cpm/pmol). The reaction was initiated by the addition of pol δ and PCNA. After 10 to 30 minutes, the reaction was terminated by the addition of 20 mM EDTA. Aliquots of reaction mixtures were spotted on DE81 ion exchange membranes followed by washing three times with 0.3 M ammonium formate (pH 7.8) and once with 95% ethanol. [3H]dTMP incorporation was read on liquid scintillation counter. Experiment was performed in triplicates. [$^3$H]dTMP incorporation was quantified by scintillation counter.

The primer extension assays were conducted as previously reported[18]. Sequences for 25-mer primer oligonucleotide and four different 40-mer oligonucleotide templates are as follows:

```
25-mer:
5'-GCC ACT ACA GCA CCT TGA CAG CCA G-3'

40-mer (G):
5'-TCA TCG GTC G CA TCG CTG GCT GTC AAG GTG CTG

TAG TGG C-3'

40-mer (C):
5'-TCA TCG GTC G CA TCC CTG GCT GTC AAG GTG CTG

TAG TGG C-3'

40-mer (A):
5'-TCA TCG GTC G CA TCA CTG GCT GTC AAG GTG CTG

TAG TGG C-3'

40-mer (T):
5'-TCA TCG GTC G CA TCT CTG GCT GTC AAG GTG CTG

TAG TGG C-3'
```

Briefly, the standard reaction mixture contained 5 μM dNTP, 5 mM MgCl2, 50 mM Tris-HCl (pH 7.5), 2 mM dithiothreitol, 100 mg/ml BSA, 50 mM NaCl, 20 nM primer/template, 50 nM PCNA, 10 nM Pol δ and variable concentrations of inhibitors. The reactions were initiated by addition of dNTPs and MgCl$_2$. Reaction was allowed to proceed at 25° C. for 2 min before addition of stop buffer (95% formamide/25 mM EDTA). The products were separated on a 20% polyacrylamide gels urea. Products was visualized on phosphorimager and quantitated using Image-J software. For single nucleotide primer extension assay[18], the protocol is identical to primer extension assay except a single dNTP is used.

Cell Proliferation Assay-MTT Method.

Human cancer cells ($5\times10^3$-$7.5\times10^3$) were initially seeded in 96-well plates (Cellstar) containing 0.2 ml media per well. After 24 hrs, these cells were treated with variable concentrations drug combinations for 48-72 hrs. Subsequently, 4,5-dimethylthiazol-2-yl-2,5-diphenyltetrazolium bromide (MTT) (20 µl of 5 mg/ml) was added to each well for 3 hrs. Formazan crystals were then dissolved in 150 µl DMSO and optical density was read at 490 nm[25]. All experiments were performed in triplicates. Results were analyzed by GraphPad Prism. Data represent mean value±SEM for each concentration of inhibitor combinations.

DNA Fiber Fluorography Dual Labeling

To analyze the effect of zelpolib, DNA fiber fluorography was used with dual labeling technique as reported. Cells were seeded in 6-well plates (Cellstar) and allowed to attach for 24 hours before pulse labeled with 25 µM IdU for 20 min. Subsequently, cells were washed three times with PBS and pulse labeled with 250 µM of CldU (Sigma) for 60 min in the presence or absence of zelpolib. Cell lysis and fiber spreading were conducted according to Schwab & Niedzwiedz. IdU and CldU were detected by primary mouse anti-BrdU antibody (BD biosciences, 1:25) and rat anti-BrdU antibody (Abcam, 1:200) and secondary fluorescent antibodies Alexa anti-mouse 594 (ThermoFisher scientific, 1:625) and Alexa anti-rat 488 (ThermoFisher scientific, 1:200). DNA fibers were imaged on fluorescence microscope and fiber lengths were measured using Image-J software. Statistics were calculated using GraphPad prism software.

Fluorescence Based Double Strand Break Repair Assay

The efficacy of homologous recombination was analyzed by a two-plasmids system according to published protocol[34,35]. HEK 293T cells ($0.15\times106$ cells/ml) were seeded in 6-well plate allowed to recover for 24 hours before being transfected with 1.5 µg of pDRGFP and pCBASceI (1:1) plasmids using Lipofectamine 3000 (Invitrogen). After 4 hours, separate wells treated with different concentrations of zelpolib or DMSO alone for 44 hours. Resulting cells were washed three times in ice cold 1×PBS and trypsinized. Cellular fluorescence for GFP was measured by flow cytometry (Beckman coulter, MoFlo XDP). About 32,000 cells were analyzed per sample. Transfection efficacy was estimated with a GFP plasmid (Invitrogen) under identical conditions. The experiment was repeated three more times and statistics were calculated using GraphPad prism software.

Further embodiments in accordance with the present application are provided below.

In at least one embodiment, a structural fold as exemplified in FIG. 12 is provided. Specifically, FIG. 12 shows a structural fold of inhibitors of DNA polymerase δ. R1 represent chemical moieties that can form hydrogen bond(s) with nucleotide bases that include adenine, thymine, guanine, and cytosine. R2 represents chemical moieties with molecular weight less than 200 Da that include but are not limited to a phenyl group.

In one or more embodiments, one or more compounds that inhibit DNA polymerases are provided, as depicted for example in FIG. 13. FIG. 13 displays the chemical structures of several derivative compounds (molecules 1-7) of the parental fold of FIG. 12.

In one or more embodiments, one or more derivatives of zelpolib as exemplified in FIG. 14 are provided. FIG. 14 displays the chemical structure of derivatives of zelpolib, where R3, R4, and R5 represent a substitution for hydrogen. In one or more embodiments, the substitution for hydrogen at R3, R4, and/or R5 is a fluoro group, a chloro group, a bromo group, a nitro group, and a sulfo group. In one or more embodiments, at least one of R3, R4, and R5 is not hydrogen.

In one or more embodiments, one or more derivatives of zelpolib as exemplified in FIG. 15 are provided. FIG. 15 displays the chemical structures of several derivative compounds (compounds 8-11) of zelpolib.

In at least one embodiment, a method for treating cancer is provided which comprises administering to a patient with cancer a therapeutically effective amount of one or more compounds of the present application, including zelpolib and/or one or more zelpolib derivatives. In at least one further aspect, the one or more compounds are administered in combination with at least one additional chemotherapeutic agent.

In one or more embodiments, a method for inhibiting cell growth is provided comprising contacting a cell with one or more compounds of the present application including zelpolib and/or one or more zelpolib derivatives. In at least one embodiment, the cell growth is inhibited in vitro. In at least one embodiment, the cell growth is inhibited in vivo.

In one or more embodiments, a method for inhibiting DNA polymerase activity is provided in which a DNA polymerase is contacted with one or more compounds of the present application, including zelpolib and/or one or more zelpolib derivatives. In at least one embodiment, the DNA polymerase is Pol δ.

In at least one embodiment, a method of inhibiting DNA replication in a cell is provided, in which a cell is contacted with one or more compounds of the present application, including zelpolib and/or one or more zelpolib derivatives. In one or more embodiments, a method of inhibiting DNA repair in a cell is provided in which a cell is contacted with one or more compounds of the present application, including zelpolib and/or one or more zelpolib derivative.

In at least one embodiment, a method for treating cancer is provided. The method comprises administering to a patient with cancer a drug that targets PD-1 or PD-L1— which includes but is not limited to pembrolizumab, nivolumab, cemiplimab, atexolizumab, or durvalumab—in combination with a therapeutically effective amount of one or more compounds of the present application, including zelpolib and/or one or more zelpolib derivatives.

In one or more embodiments, a method for treating cancer is provided. In particular, in the one or more embodiments, the method comprises administering to a patient with cancer a drug that targets CTLA-4, which includes but is not limited to iplimumab. The drug that targets CTLA-4 is administered in combination with a therapeutically effective amount of one or more compounds of the present application, including zelpolib and/or one or more zelpolib derivatives.

In at least one embodiment, another method for treating cancer is provided. The method comprises administering to a patient with cancer a drug that targets DNA repair pathway by PARP inhibitors, which includes but is not limited to olaparib, rucaparib, or niraparib. The drug that targets DNA repair pathway by PARP inhibitors is administered in combination with a therapeutically effective amount of one or more compounds of the present application, including zelpolib and/or one or more zelpolib derivatives.

In one or more embodiments, a method for treating autoimmune rheumatoid arthritis due to proliferation of immune cells is provided. In at least one embodiment, the method comprises administering a therapeutically effective amount of one or more compounds of the present application, including zelpolib and/or one or more zelpolib derivatives. In at least one embodiment, the method comprises administering a therapeutically effective amount of one or more compounds of the present application (e.g., zelpolib and/or one or more zelpolib derivatives) in combination with methotreaxate.

In one or more embodiments, a method for treating autoimmune psoriasis due to proliferation of immune cells is provided. In at least one embodiment, the method comprises administering a therapeutically effective amount of one or more compounds of the present application, including zelpolib and/or one or more zelpolib derivatives. In at least one embodiment, the method comprises administering a therapeutically effective amount of one or more compounds of the present application (e.g., zelpolib and/or one or more zelpolib derivatives) in combination with small molecule immune suppressants In one or more embodiments, a method for treating autoimmune rheumatoid arthritis due to proliferation of immune cells is provided. In at least one embodiment, the method comprises administering a therapeutically effective amount of one or more compounds of the present application, including zelpolib and/or one or more zelpolib derivatives, in combination with one or more tumor-necrosis-factor inhibitors that include but are not limited to adalimumab. In at least one embodiment, the method comprises administering a therapeutically effective amount of one or more compounds of the present application (e.g., zelpolib and/or one or more zelpolib derivatives) in combination with one or more JAK inhibitors that include but are not limited to tofacitinib.

All references cited herein are incorporated by reference to the same extent as if each individual publication, database entry (e.g. Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g. Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents. The entire disclosure of each of the patent documents, including certificates of correction, patent application documents, scientific articles, governmental reports, websites, and other references referred to herein is incorporated by reference herein in its entirety for all purposes. In case of a conflict in terminology, the present specification controls.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

1 Karran, P. Mechanisms of tolerance to DNA damaging therapeutic drugs. *Carcinogenesis* 22, 1931-1937 (2001).

2 Wilson, P. M., Danenberg, P. V., Johnston, P. G., Lenz, H. J. & Ladner, R. D. Standing the test of time: targeting thymidylate biosynthesis in cancer therapy. *Nature reviews. Clinical oncology* 11, 282-298, doi:10.1038/nrclinonc.2014.51 (2014).

3 Delgado, J. L., Hsieh, C. M., Chan, N. L. & Hiasa, H. Topoisomerases as anticancer targets. *Biochem J* 475, 373-398, doi:10.1042/bcj20160583 (2018).

4 Nitiss, J. L. DNA topoisomerases in cancer chemotherapy: using enzymes to generate selective DNA damage. *Current opinion in investigational drugs* (London, England: 2000) 3, 1512-1516 (2002).

5 Nitiss, J. L. Targeting DNA topoisomerase II in cancer chemotherapy. *Nature reviews. Cancer* 9, 338-350, doi:10.1038/nrc2607 (2009).

6 Cheung-Ong, K., Giaever, G. & Nislow, C. DNA-damaging agents in cancer chemotherapy: serendipity and chemical biology. *Chemistry & biology* 20, 648-659, doi:10.1016/j.chembiol.2013.04.007 (2013).

7 Tiwari, M. Antimetabolites: established cancer therapy. *Journal of cancer research and therapeutics* 8, 510-519, doi:10.4103/0973-1482.106526 (2012).

8 Hagner, N. & Joerger, M. Cancer chemotherapy: targeting folic acid synthesis. *Cancer management and research* 2, 293-301, doi:10.2147/cmr.s10043 (2010).

9 Shao, J., Liu, X., Zhu, L. & Yen, Y. Targeting ribonucleotide reductase for cancer therapy. *Expert opinion on therapeutic targets* 17, 1423-1437, doi:10.1517/14728222.2013.840293 (2013).

10 Collins, I., Weber, A. & Levens, D. Transcriptional consequences of topoisomerase inhibition. *Mol Cell Biol* 21, 8437-8451, doi:10.1128/mcb.21.24.8437-8451.2001 (2001).

11 Pommier, Y. Drugging topoisomerases: lessons and challenges. *ACS chemical biology* 8, 82-95, doi:10.1021/cb300648v (2013).

12 Doublie, S. & Zahn, K. E. Structural insights into eukaryotic DNA replication. *Frontiers in microbiology* 5, 444, doi:10.3389/fmicb.2014.00444 (2014).

13 Zhang, D. & O'Donnell, M. The Eukaryotic Replication Machine. *The Enzymes* 39, 191-229, doi:10.1016/bs.enz.2016.03.004 (2016).

14 Johansson, E. & Macneill, S. A. The eukaryotic replicative DNA polymerases take shape. *Trends in biochemical sciences* 35, 339-347, doi:10.1016/j.tibs.2010.01.004 (2010).

15 Irwin, J. J. Using ZINC to acquire a virtual screening library. *Current protocols in bioinformatics/editoral board, Andreas D. Baxevanis . . . [et al.]* Chapter 14, Unit 14 16, doi:10.1002/0471250953.bi1406s22 (2008).

16 Zhang, P. et al. Expression of the catalytic subunit of human DNA polymerase delta in mammalian cells using a vaccinia virus vector system. *J Biol Chem* 270, 7993-7998 (1995).

17 Meng, X., Zhou, Y., Lee, E. Y., Lee, M. Y. & Frick, D. N. The p12 subunit of human polymerase delta modulates the rate and fidelity of DNA synthesis. Biochemistry 49, 3545-3554, doi:10.1021/bi100042b (2010).

18 Meng, X. et al. DNA damage alters DNA polymerase delta to a form that exhibits increased discrimination against modified template bases and mismatched primers. *Nucleic Acids Res* 37, 647-657, doi:10.1093/nar/gkn1000 (2009).

19 Wu, P., Nielsen, T. E. & Clausen, M. H. FDA-approved small-molecule kinase inhibitors. *Trends in pharmacological sciences* 36, 422-439, doi:10.1016/j.tips.2015.04.005 (2015).

20 Ledermann, J. et al. Olaparib maintenance therapy in patients with platinum-sensitive relapsed serous ovarian cancer: a preplanned retrospective analysis of outcomes by BRCA status in a randomised phase 2 trial. *The Lancet. Oncology* 15, 852-861, doi:10.1016/s1470-2045(14)70228-1 (2014).

21 George Paul, A., Sharma-Walia, N., Kerur, N., White, C. & Chandran, B. Piracy of prostaglandin E2/EP receptor-mediated signaling by Kaposi's sarcoma-associated herpes virus (HHV-8) for latency gene expression: strategy of a successful pathogen. *Cancer research* 70, 3697-3708, doi:10.1158/0008-5472.can-09-3934 (2010).

22 Salic, A. & Mitchison, T. J. A chemical method for fast and sensitive detection of DNA synthesis in vivo. *Proc Natl Acad Sci USA* 105, 2415-2420, doi:10.1073/pnas.0712168105 (2008).

23 Buck, S. B. et al. Detection of S-phase cell cycle progression using 5-ethynyl-2'-deoxyuridine incorporation with click chemistry, an alternative to using 5-bromo-2'-deoxyuridine antibodies. *BioTechniques* 44, 927-929, doi:10.2144/000112812 (2008).

24 Schwab, R. A. & Niedzwiedz, W. Visualization of DNA replication in the vertebrate model system DT40 using the DNA fiber technique. *Journal of visualized experiments: JoVE*, e3255, doi:10.3791/3255 (2011).

25 Twentyman, P. R. & Luscombe, M. A study of some variables in a tetrazolium dye (MTT) based assay for cell growth and chemosensitivity. *British journal of cancer* 56, 279-285 (1987).

26 Wong, S. J., Myette, M. S., Wereley, J. P. & Chitambar, C. R. Increased sensitivity of hydroxyurea-resistant leukemic cells to gemcitabine. *Clinical cancer research: an official journal of the American Association for Cancer Research* 5, 439-443 (1999).

27 Kuriyama, I. et al. Effect of dehydroaltenusin-C12 derivative, a selective DNA polymerase alpha inhibitor, on DNA replication in cultured cells. *Molecules* (Basel, Switzerland) 13, 2948-2961, doi:10.3390/molecules13122948 (2008).

28 McBurney, M. W. & Whitmore, G. F. Mechanism of growth inhibition by methotrexate. *Cancer research* 35, 586-590 (1975).

29 Mitchell, E. P. Oxaliplatin with 5-FU or as a single agent in advanced/metastatic colorectal cancer. *Oncology* (Williston Park, N.Y.) 14, 30-32 (2000).

30 Brennan, M. J. & Vaitkevicius, V. K. 5-Fluorouracil in clinical cancer experience with 155 patients. *Cancer chemotherapy reports* 6, 8-11 (1960).

31 Gold, G. L. et al. A clinical study of 5-fluorouracil. *Cancer research* 19, 935-939 (1959).

32 Lee, M., Wang, X., Zhang, S., Zhang, Z. & Lee, E. Y. C. Regulation and Modulation of Human DNA Polymerase delta Activity and Function. *Genes* 8, doi:10.3390/genes8070190 (2017).

33 Maloisel, L., Fabre, F. & Gangloff, S. DNA polymerase delta is preferentially recruited during homologous recombination to promote heteroduplex DNA extension. *Mol Cell Biol* 28, 1373-1382, doi:10.1128/mcb.01651-07 (2008).

34 Nakanishi, K., Cavallo, F., Brunet, E. & Jasin, M. Homologous recombination assay for interstrand cross-link repair. *Methods Mol Biol* 745, 283-291, doi:10.1007/978-1-61779-129-1_16 (2011).

35 Weinstock, D. M., Nakanishi, K., Helgadottir, H. R. & Jasin, M. Assaying double-strand break repair pathway choice in mammalian cells using a targeted endonuclease or the RAG recombinase. *Methods in enzymology* 409, 524-540, doi:10.1016/s0076-6879(05)09031-2 (2006).

36 Ahrabi, S. et al. A role for human homologous recombination factors in suppressing microhomology-mediated end joining. *Nucleic Acids Res* 44, 5743-5757, doi:10.1093/nar/gkw326 (2016).

37 De Picciotto, N., Cacheux, W., Roth, A., Chappuis, P. O. & Labidi-Galy, S. I. Ovarian cancer: Status of homologous recombination pathway as a predictor of drug response. *Critical reviews in oncology/hematology* 101, 50-59, doi:10.1016/j.critrevonc.2016.02.014 (2016).

38 Kim, G. et al. FDA Approval Summary: Olaparib Monotherapy in Patients with Deleterious Germline BRCA-Mutated Advanced Ovarian Cancer Treated with Three or More Lines of Chemotherapy. *Clinical cancer research: an official journal of the American Association for Cancer Research* 21, 4257-4261, doi:10.1158/1078-0432.ccr-15-0887 (2015).

39 Meehan, R. S. & Chen, A. P. New treatment option for ovarian cancer: PARP inhibitors. *Gynecologic oncology research and practice* 3, 3, doi:10.1186/s40661-016-0024-7 (2016).

40 Moore, D. C., Ringley, J. T. & Patel, J. Rucaparib: A Poly(ADP-Ribose) Polymerase Inhibitor for BRCA-Mutated Relapsed Ovarian Cancer. *Journal of pharmacy practice*, 897190017743131, doi:10.1177/0897190017743131 (2017).

41 Taylor, K. N. & Eskander, R. N. PARP inhibitors in epithelial ovarian cancer. *Recent patents on anti-cancer drug discovery*, doi:10.2174/1574892813666171204094822 (2017).

42 Scott, L. J. Niraparib: First Global Approval. *Drugs* 77, 1029-1034, doi:10.1007/s40265-017-0752-y (2017).

43 Syed, Y. Y. Rucaparib: First Global Approval. *Drugs* 77, 585-592, doi:10.1007/s40265-017-0716-2 (2017).

44 Hanahan, D. & Weinberg, R. A. The hallmarks of cancer. *Cell* 100, 57-70 (2000).

45 Hanahan, D. & Weinberg, R. A. Hallmarks of cancer: the next generation. *Cell* 144, 646-674, doi:10.1016/j.cell.2011.02.013 (2011).

46 Arora, A. & Scholar, E. M. Role of tyrosine kinase inhibitors in cancer therapy. *The Journal of pharmacology and experimental therapeutics* 315, 971-979, doi:10.1124/jpet.105.084145 (2005).

47 Gotink, K. J. & Verheul, H. M. Anti-angiogenic tyrosine kinase inhibitors: what is their mechanism of action? *Angiogenesis* 13, 1-14, doi:10.1007/s10456-009-9160-6 (2010).

48 Todd, R. C. & Lippard, S. J. Inhibition of transcription by platinum antitumor compounds. *Metallomics: integrated biometal science* 1, 280-291, doi:10.1039/b907567d (2009).

49 Sonohara, Y., Iwai, S. & Kuraoka, I. An in vitro method for detecting genetic toxicity based on inhibition of RNA synthesis by DNA lesions. *Genes and environment: the official journal of the Japanese Environmental Mutagen Society* 37, 8, doi:10.1186/s41021-015-0014-8 (2015).

50 Ward, J., Kapadia, K., Brush, E. & Salhanick, S. D. Amatoxin poisoning: case reports and review of current therapies. *The Journal of emergency medicine* 44, 116-121, doi:10.1016/j.jemermed.2012.02.020 (2013).

51 Allen, B., Desai, B. & Lisenbee, N. Amatoxin: A Review. *ISRN Emergency Medicine* 2012, 4, doi:10.5402/2012/190869 (2012).

52 Boussios, S., Pentheroudakis, G., Katsanos, K. & Pavlidis, N. Systemic treatment-induced gastrointestinal toxicity: incidence, clinical presentation and management. *Annals of gastroenterology* 25, 106-118 (2012).

53 Damia, G. et al. Activity of aphidicolin glycinate alone or in combination with cisplatin in a murine ovarian tumor resistant to cisplatin. *Cancer chemotherapy and pharmacology* 30, 459-464 (1992).

54 Moreland, N. J., Illand, M., Kim, Y. T., Paul, J. & Brown, R. Modulation of drug resistance mediated by loss of mismatch repair by the DNA polymerase inhibitor aphidicolin. *Cancer research* 59, 2102-2106 (1999).

55 O'Dwyer, P. J. et al. Antitumor activity and biochemical effects of aphidicolin glycinate (NSC 303812) alone and in combination with cisplatin in vivo. *Cancer research* 54, 724-729 (1994).

56 Sargent, J. M., Elgie, A. W., Williamson, C. J. & Taylor, C. G. Aphidicolin markedly increases the platinum sensitivity of cells from primary ovarian tumours. *British journal of cancer* 74, 1730-1733 (1996).

57 Sessa, C. et al. Phase I and clinical pharmacological evaluation of aphidicolin glycinate. *Journal of the National Cancer Institute* 83, 1160-1164 (1991).

58 Leeds, J. M. & Mathews, C. K. Cell cycle-dependent effects on deoxyribonucleotide and DNA labeling by nucleoside precursors in mammalian cells. *Mol Cell Biol* 7, 532-534 (1987).

59 Leeds, J. M., Slabaugh, M. B. & Mathews, C. K. DNA precursor pools and ribonucleotide reductase activity: distribution between the nucleus and cytoplasm of mammalian cells. *Mol Cell Biol* 5, 3443-3450 (1985).

60 Momparler, R. L. Biochemical pharmacology of cytosine arabinoside. *Medical and pediatric oncology* 10 Suppl 1, 45-48 (1982).

61 Perrino, F. W. & Mekosh, H. L. Incorporation of cytosine arabinoside monophosphate into DNA at internucleotide linkages by human DNA polymerase alpha. *J Biol Chem* 267, 23043-23051 (1992).

62 Dietlein, F., Thelen, L. & Reinhardt, H. C. Cancer-specific defects in DNA repair pathways as targets for personalized therapeutic approaches. *Trends in genetics: TIG* 30, 326-339, doi:10.1016/j.tig.2014.06.003 (2014).

63 Prakash, R., Zhang, Y., Feng, W. & Jasin, M. Homologous recombination and human health: the roles of BRCA1, BRCA2, and associated proteins. *Cold Spring Harbor perspectives in biology* 7, a016600, doi:10.1101/cshperspect.a016600 (2015).

64 Eshleman, J. R. & Markowitz, S. D. Mismatch repair defects in human carcinogenesis. *Human molecular genetics* 5 Spec No, 1489-1494 (1996).

65 Boland, C. R. & Goel, A. Microsatellite instability in colorectal cancer. *Gastroenterology* 138, 2073-2087 e2073, doi:10.1053/j.gastro.2009.12.064 (2010).

66 Konstantinopoulos, P. A., Ceccaldi, R., Shapiro, G. I. & D'Andrea, A. D. Homologous Recombination Deficiency: Exploiting the Fundamental Vulnerability of Ovarian Cancer. *Cancer discovery* 5, 1137-1154, doi:10.1158/2159-8290.cd-15-0714 (2015).

67 Caruso, D. et al. Niraparib in ovarian cancer: results to date and clinical potential. *Therapeutic advances in medical oncology* 9, 579-588, doi:10.1177/1758834017718775 (2017).

68 Chang, L., Chang, M., Chang, H. M. & Chang, F. Microsatellite Instability: A Predictive Biomarker for Cancer Immunotherapy. *Applied immunohistochemistry & molecular morphology: AIMM* 26, e15-e21, doi:10.1097/pai.0000000000000575 (2018).

69 First Tissue-Agnostic Drug Approval Issued. *Cancer discovery* 7, 656, doi:10.1158/2159-8290.cd-nb2017-078 (2017).

70 McVey, M., Khodaverdian, V. Y., Meyer, D., Cerqueira, P. G. & Heyer, W. D. Eukaryotic DNA Polymerases in Homologous Recombination. *Annual review of genetics* 50, 393-421, doi:10.1146/annurev-genet-120215-035243 (2016).

71 Longley, M. J., Pierce, A. J. & Modrich, P. DNA polymerase delta is required for human mismatch repair in vitro. *J Biol Chem* 272, 10917-10921 (1997).

72 Swan, M. K., Johnson, R. E., Prakash, L., Prakash, S. & Aggarwal, A. K. Structural basis of high-fidelity DNA synthesis by yeast DNA polymerase delta. *Nat Struct Mol Biol* 16, 979-986, doi:10.1038/nsmb.1663 (2009).

73 Guex, N. & Peitsch, M. C. SWISS-MODEL and the Swiss-PdbViewer: an environment for comparative protein modeling. *Electrophoresis* 18, 2714-2723, doi:10.1002/elps.1150181505 (1997).

74 Lipinski, C. A., Lombardo, F., Dominy, B. W. & Feeney, P. J. Experimental and computational approaches to estimate solubility and permeability in drug discovery and development settings. *Advanced drug delivery reviews* 46, 3-26 (2001).

75 Allen, W. J. et al. DOCK 6: Impact of new features and current docking performance. *Journal of computational chemistry* 36, 1132-1156, doi:10.1002/jcc.23905 (2015).

76 Mezencev, R., Matyunina, L. V., Wagner, G. T. & McDonald, J. F. Acquired resistance of pancreatic cancer cells to cisplatin is multifactorial with cell context-dependent involvement of resistance genes. *Cancer gene therapy* 23, 446-453, doi:10.1038/cgt.2016.71 (2016).

77 Coley, H. M. Development of drug-resistant models. *Methods in molecular medicine* 88, 267-273 (2004).

What is claimed is:

1. A method of inhibiting cell growth, the method comprising:
  contacting a cell with a compound, wherein the compound comprises zelpolib, a derivative of zelpolib, or a pharmaceutically acceptable salt of zelpolib, wherein the derivative of zelpolib is selected from the group consisting of compounds 8-10:

8

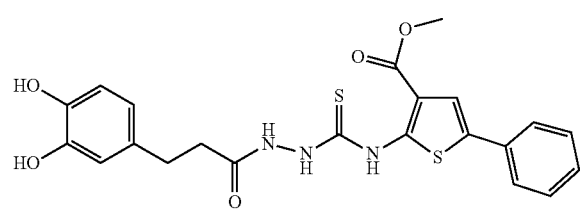

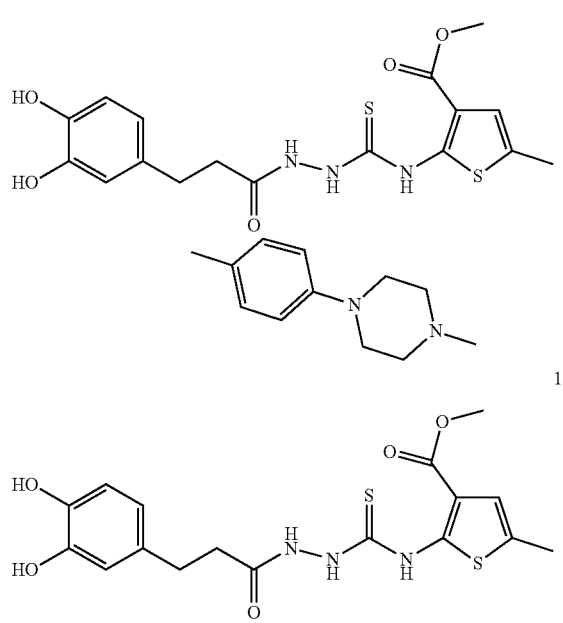

9

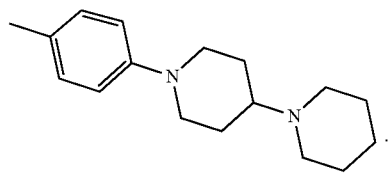

-continued

2. The method of claim 1, wherein the cell growth is inhibited in vivo.

3. The method of claim 1, wherein the cell growth is inhibited in vitro.

4. The method of claim 1, wherein the cell is a cancer cell.

5. A method for inhibiting DNA polymerase activity, the method comprising:

contacting a DNA polymerase with a compound, wherein the compound comprises zelpolib, a derivative of zelpolib, or a pharmaceutically acceptable salt of zelpolib, wherein the derivative of zelpolib is selected from the group consisting of compounds 8-10:

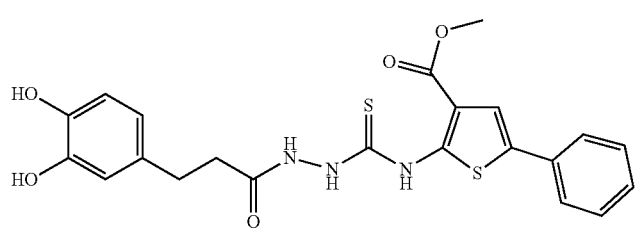

8

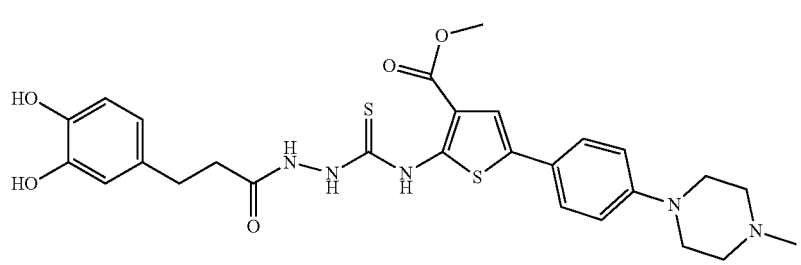

9

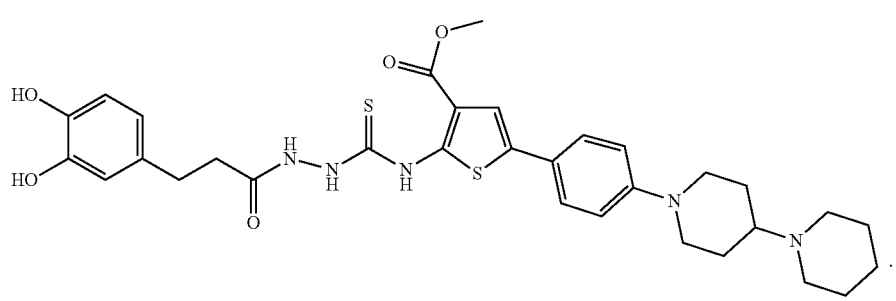

10

6. The method of claim 5, wherein the DNA polymerase is Pol δ.

7. The method of claim 6, wherein the activity of Pol δ is inhibited in vitro.

8. The method of claim 6, wherein activity of Pol δ is inhibited in vivo.

9. A method for inhibiting DNA replication and DNA repair in a cell, the method comprising:
contacting a cell with a compound, wherein the compound comprises zelpolib, a derivative of zelpolib, or a pharmaceutically acceptable salt of zelpolib, wherein the derivative of zelpolib is represented by the following formula:

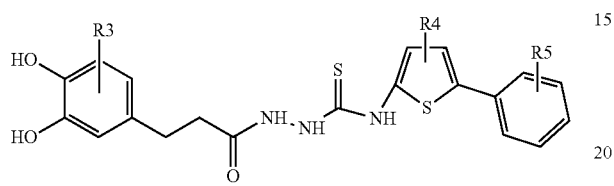

wherein R3, R4, and R5 is hydrogen, or a substitution for hydrogen selected from the group consisting of: a fluoro group, a chloro group, a bromo group, a nitro group, and a sulfo group; and wherein at least one of R3, R4, and R5 is not hydrogen.

10. The method of claim 9, wherein DNA replication and repair is inhibited in the cell in vivo.

11. The method of claim 9, wherein DNA replication and repair is inhibited in the cell in vitro.

12. The method of claim 9, wherein the cell is a cancer cell.

* * * * *

UNITED STATES PATENT AND TRADEMARK OFFICE
CERTIFICATE OF CORRECTION

| | | |
|---|---|---|
| PATENT NO. | : 11,324,720 B2 | |
| APPLICATION NO. | : 16/659283 | |
| DATED | : May 10, 2022 | |
| INVENTOR(S) | : Zhongtao Zhang et al. | |

It is certified that error appears in the above-identified patent and that said Letters Patent is hereby corrected as shown below:

On the Title Page

Item (12), delete "Zhang" and insert -- Zhang et al. --

Item (72) Inventor, beginning Line 1:
"Zhongtao Zhang, Valhalla, NY (US)" should read -- Dr. Zhongtao Zhang, Haworth, NJ (US), Dr. Bhanvi Mishra, Burlington, MA (US), Dr. Sufang Zhang, Briarcliff Manor, NY (US), Dr. Marietta Lee, Peekskill, NY (US) --

Signed and Sealed this
Twelfth Day of September, 2023

Katherine Kelly Vidal
*Director of the United States Patent and Trademark Office*